US010653493B2

(12) United States Patent
Schneider

(10) Patent No.: US 10,653,493 B2
(45) Date of Patent: *May 19, 2020

(54) SURGICAL GLOVE SYSTEMS AND METHOD OF USING THE SAME

(71) Applicant: Andrew I. Schneider, Palm Beach Gardens, FL (US)

(72) Inventor: Andrew I. Schneider, Palm Beach Gardens, FL (US)

(*) Notice: Subject to any disclaimer, the term of this patent is extended or adjusted under 35 U.S.C. 154(b) by 816 days.

This patent is subject to a terminal disclaimer.

(21) Appl. No.: 15/255,851

(22) Filed: Sep. 2, 2016

(65) Prior Publication Data

US 2017/0042627 A1 Feb. 16, 2017

Related U.S. Application Data

(63) Continuation of application No. 14/875,223, filed on Oct. 5, 2015, which is a continuation-in-part of
(Continued)

(51) Int. Cl.
*A61B 18/14* (2006.01)
*A61B 42/10* (2016.01)
(Continued)

(52) U.S. Cl.
CPC .............. *A61B 42/10* (2016.02); *A61B 18/14* (2013.01); *A61B 42/00* (2016.02); *A61B 46/00* (2016.02);
(Continued)

(58) Field of Classification Search
CPC ... A61B 19/04; A61B 19/041; A61B 19/5202; A61B 2218/007; A61B 2218/002; A61B 2018/00595; A61B 42/10
See application file for complete search history.

(56) References Cited

U.S. PATENT DOCUMENTS 2,311,276 A 2/1943 Wilcox
2,847,012 A 8/1958 Eastman
(Continued)

FOREIGN PATENT DOCUMENTS

DE 102005031082 1/2007
GB 2316429 * 2/1998 ............ A41D 19/00
(Continued)

*Primary Examiner* — Jaymi E Della
(74) *Attorney, Agent, or Firm* — Duane Morris LLP; J. Rodman Steele, Jr.; Gregory M. Lefkowitz

(57) ABSTRACT

A surgical system that includes a surgical glove configured to be removably attached to a human hand is disclosed. The surgical glove can include a first surgical instrument attached to the surgical glove, where the first surgical instrument is nonremoveably, integrally attached to the surgical glove during the formation of the surgical glove, and where the first surgical instrument is coupled to a finger of the surgical glove; a first switch attached to the surgical glove for controlling the first surgical support system; and a first actuating element attached to a thumb of the surgical glove. The first actuating element can be a discrete element. The first switch can be actuated when the first actuating element is placed in close proximity to the first switch, and a thumb of said surgical glove can be free of surgical support systems.

12 Claims, 15 Drawing Sheets

Related U.S. Application Data application No. 13/626,733, filed on Sep. 25, 2012, now Pat. No. 9,149,337, which is a continuation-in-part of application No. 13/450,958, filed on Apr. 19, 2012, now Pat. No. 8,449,541, which is a continuation of application No. 13/081,345, filed on Apr. 6, 2011, now Pat. No. 8,182,479, which is a continuation of application No. 11/591,305, filed on Nov. 1, 2006, now Pat. No. 7,931,648, which is a continuation-in-part of application No. 11/335,050, filed on Jan. 19, 2006, now Pat. No. 7,951,145.

(60) Provisional application No. 61/539,350, filed on Sep. 26, 2011.

(51) Int. Cl.
    *A61B 90/30*       (2016.01)
    *A61B 42/00*       (2016.01)
    *A61B 46/00*       (2016.01)
    *A61B 18/00*       (2006.01)
    *A61B 17/32*       (2006.01)
    *A61B 34/00*       (2016.01)

(52) U.S. Cl.
CPC .... *A61B 90/30* (2016.02); *A61B 2017/32007* (2017.08); *A61B 2017/320069* (2017.08); *A61B 2018/00589* (2013.01); *A61B 2018/00595* (2013.01); *A61B 2034/741* (2016.02); *A61B 2090/306* (2016.02); *A61B 2090/309* (2016.02); *A61B 2218/002* (2013.01); *A61B 2218/007* (2013.01)

(56) References Cited

U.S. PATENT DOCUMENTS

| | | | |
|---|---|---|---|
| 3,735,760 A | 5/1973 | Vreeland, Jr. | |
| 3,845,771 A | 11/1974 | Vise | |
| 3,875,945 A | 4/1975 | Friedman | |
| 4,198,985 A | 4/1980 | Abel | |
| 4,337,496 A | 6/1982 | Laird | |
| 4,488,726 A | 12/1984 | Murray | |
| 4,510,939 A | 4/1985 | Brenman et al. | |
| 4,620,528 A | 11/1986 | Arraval | |
| 4,932,952 A | 6/1990 | Wojciechowicz, Jr. | |
| 5,120,304 A | 6/1992 | Sasaki | |
| 5,242,440 A | 9/1993 | Shippert | |
| 5,255,167 A * | 10/1993 | Toussaint | F21L 4/06 359/354 |
| 5,273,524 A | 12/1993 | Fox et al. | |
| 5,283,722 A | 2/1994 | Koenen et al. | |
| 5,312,400 A | 5/1994 | Bales et al. | |
| 5,673,436 A | 10/1997 | Piper | |
| 5,776,126 A | 7/1998 | Wilk et al. | |
| 5,782,516 A | 7/1998 | Partida | |
| 5,816,676 A * | 10/1998 | Koenen Myers | A61B 42/10 362/8 |
| 5,947,922 A | 9/1999 | Macleod | |
| 6,112,330 A | 9/2000 | Bryan | |
| 6,409,734 B1 | 6/2002 | Zapata | |
| 6,551,312 B2 | 4/2003 | Zhang et al. | |
| 6,567,990 B1 | 5/2003 | Spitznagle | |
| 6,569,163 B2 | 5/2003 | Hata et al. | |
| 6,592,235 B1 | 7/2003 | Mayo | |
| 6,646,855 B2 | 11/2003 | Buening et al. | |
| 6,892,397 B2 | 5/2005 | Raz et al. | |
| 7,012,797 B1 | 3/2006 | Delida | |
| 2001/0039415 A1 | 11/2001 | Francischelli et al. | |
| 2003/0235048 A1 | 12/2003 | Gyori | |
| 2004/0154071 A1 | 8/2004 | Frahm | |
| 2004/0260281 A1* | 12/2004 | Baxter, III | A61B 42/10 606/41 |
| 2006/0007669 A1 | 1/2006 | Blackburn | |
| 2006/0282936 A1* | 12/2006 | Olson | A41D 19/01558 2/161.7 |
| 2013/0046302 A1 | 2/2013 | Schneider | |

FOREIGN PATENT DOCUMENTS

| | | |
|---|---|---|
| WO | 02/43550 A1 | 6/2002 |
| WO | 2010/085958 | 8/2010 |

* cited by examiner

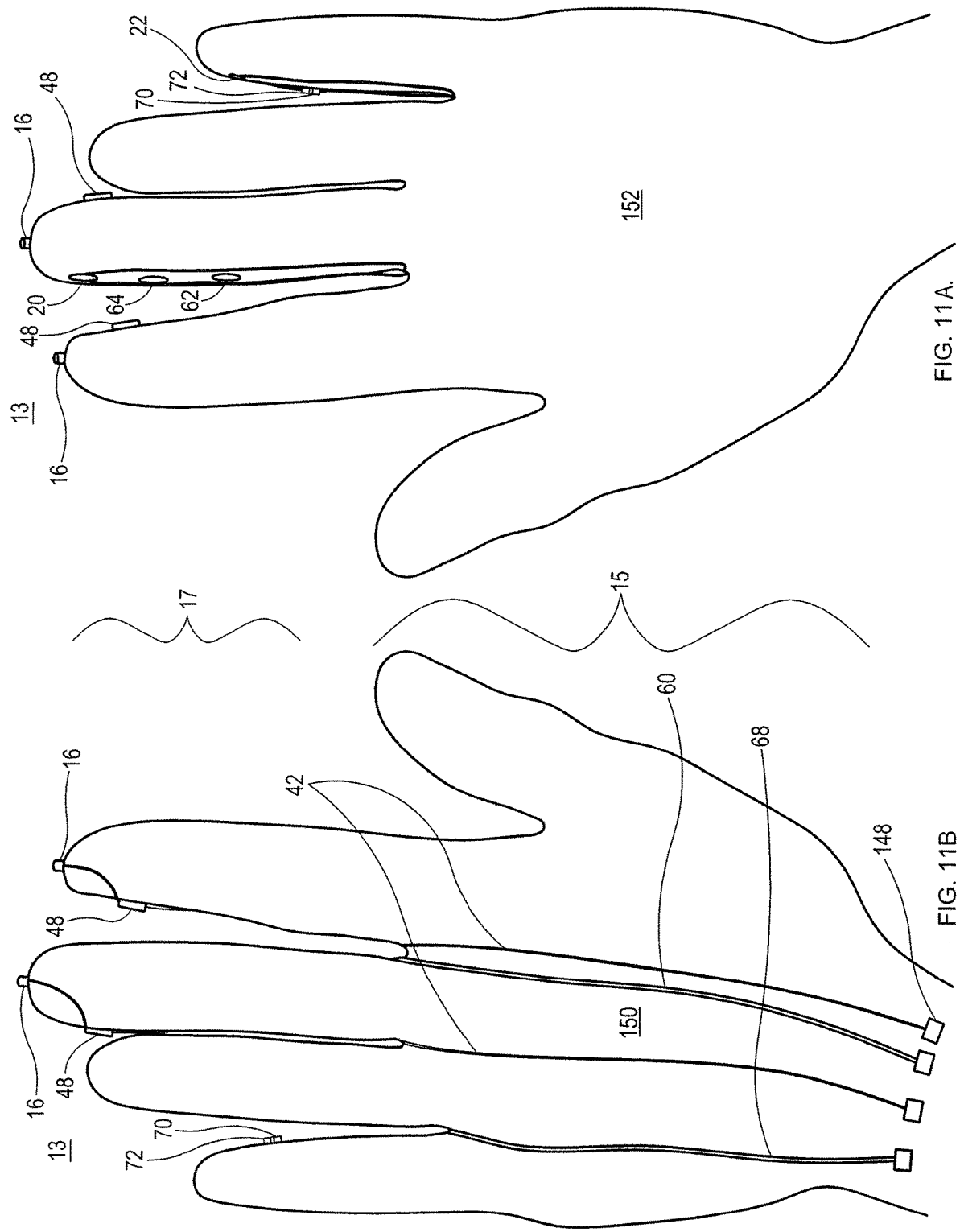

SURGICAL GLOVE SYSTEMS AND METHOD OF USING THE SAME

CROSS-REFERENCE TO RELATED APPLICATIONS

This application is a continuation application of U.S. patent application Ser. No. 14/875,223, filed Oct. 5, 2015, which is a continuation-in-part of U.S. patent application Ser. No. 13/626,733, filed Sep. 25, 2012, now U.S. Pat. No. 9,149,337, which claims priority to U.S. Provisional Application No. 61/539,350, filed Sep. 26, 2011, and is a continuation-in-part of U.S. patent application Ser. No. 13/450,958, filed Apr. 19, 2012, now U.S. Pat. No. 8,449,541, which is a continuation of U.S. patent application Ser. No. 13/081,345, filed Apr. 6, 2011, now U.S. Pat. No. 8,182,479, which is a continuation application of U.S. patent application Ser. No. 11/591,305 filed Nov. 1, 2006, now U.S. Pat. No. 7,931,648, which is a continuation-in-part of U.S. patent application Ser. No. 11/335,050, filed Jan. 19, 2006, now U.S. Pat. No. 7,951,145, the entireties of which are incorporated by reference herein.

FIELD OF THE INVENTION

This invention is directed generally to surgical systems, and more particularly to surgical systems for providing support to a surgeon during surgery.

BACKGROUND

The majority of conventional surgical instruments are hand-held and hand, foot, or remotely operated. Surgical instruments such as electrical cautery, suction, and hand-held lights typically include electrical supply cords, fiber optic cords, or conduits that are held in place on a surgical table by fastening the cords with clamps to a surgical top drape positioned on top of the patient. The cords and conduits are arranged on the surgical field so that they can be accessed easily by surgeons, assistants, or nurses. Unfortunately, as well intention and organized as the setup may be, the cords and conduits invariably become entangled during the course of a procedure, thereby creating frequent frustration and time delay. Once entangled, instruments become more difficult to easily reach or to pass between surgeons. Entanglement of instrument wire and cords also shortens the effective working length of the instruments and further interferes with their accurate and unobstructed use.

Often times, the electrical cautery or suction supply is accidentally dropped from the surgical field onto the floor, thereby compromising their sterility and requiring replacement. This occurs more frequently with shower curtains drapes and during the course of long, complex procedures.

Typically, irrigation supplies are stored on a table remote from the surgical field and are handed to the surgeon by a scrub nurse within a bulb syringe, or other container, when requested. Unfortunately, during a procedure, the scrub nurse may be occupied for a variety of reasons and have difficulty providing the irrigation in a timely fashion. For example, a scrub nurse is commonly asked to hold a retractor, or other instrument in the surgical field, and is not available to easily turn around and grab the irrigation when needed.

More recently, U.S. Pat. Nos. 7,931,648, 7,951,145 and 8,182,479 to Schneider ("Schneider Patents") disclosed surgical systems that include a glove with multiple surgical support systems attached thereto. However, there are still challenges to overcome with these systems, including instances where the suction line becomes clogged, a surgical instrument fires accidentally, or conventional surgical systems need to be used in addition to the gloves described in the Schneider Patents. Thus, there is a great need for more efficient, user-friendly systems that eliminate entanglement reliably, that allow for simultaneous use and activation of more than one integral surgical support system, and further avoids the problems set forth herein.

SUMMARY OF THE INVENTION

This invention relates to a surgical system that includes one or more surgical gloves having support systems such as, but not limited to, one or more light sources, an electrical cautery device, a suction source, and an irrigation supply. The surgical system may also include a surgical gown. Each surgical glove may include one or more of the light sources, electrical cautery devices, suction sources, and irrigation sources positioned on fingers of the surgical glove. The support systems may be controlled with switches positioned on the fingers upon which each support system is positioned. The switches may be operable with the thumb of the human hand wearing the surgical glove. The surgical system may also include a surgical gown having a connection system for attaching support conduit supporting the support systems to the surgical gown. The surgical system enables a surgeon to have a plurality of support systems immediately available and eliminates entanglement problems endemic with conventional systems. The support systems may be attached to the surgical glove(s) in various configurations to optimize the configuration for a surgeon such that the systems are located for facility of use and in a position where the systems are unlikely to obstruct or conflict with the general use of the surgeon's hand or the use of surgical instruments, and in a manner which optimizes the simultaneous, synergistic use of more than one support system.

The support systems, including, but not limited to, light sources, electrical cautery devices, suction sources, and irrigation sources, may be coupled to distal, volar, radial, ulnar or dorsal surface locations of the fingers of the surgical glove(s). In particular, in one embodiment, the light source may be coupled to a distal, dorsal surface of the glove's index or long finger, or both. The electrical cautery device may be coupled to a distal, volar end of the glove's index finger. The suction source may be coupled to a distal, volar radial end of the glove's long finger. The irrigation source may be coupled to a distal, volar radial end of the glove's little finger.

The support systems may be controlled with support control switches adapted for each support system. The support switches may be attached to the fingers of the glove upon which the support system is attached and may be easily activated using the thumb on the same hand. For instance, the electrical cautery switch may be positioned on the finger upon which the electrical cautery is attached. The electrical cautery switch may be positioned on the radial aspect of the finger of the glove.

The surgical system can also include a safety switch for controlling a cutting system so that the cutting system will not operate unless the safety switch and either the cutting or coagulating switch are actuated. The safety switch can be attached to the glove or a complementary surgical gown and positioned such that the safety switch will not be actuated except with the hand opposite that wearing the glove.

The surgical system can also include a shunt for controlling fluid flow between an irrigation conduit and a suction conduit. The shunt can be attached to the glove or a complementary surgical gown.

The surgical system can also include a safety switch for controlling a cutting system so that the cutting system will not operate unless both the cutting or coagulating switch and the safety switch are actuated. The safety switch can be attached to the glove or a complementary surgical gown and positioned such that the safety switch cannot be actuated except with the hand opposite that wearing the glove. Alternately, the safety switch can be positioned on an ulnar surface of the finger of the glove to which the cutting system is coupled and can be actuated by the finger located adjacent to the safety switch (e.g., a safety switch on the ulnar side of the index finger can be actuated by the long finger).

The surgical system can also include a shunt for controlling fluid flow between an irrigation conduit and a suction conduit. The shunt can be attached to the glove or a complementary surgical gown. The shunt can be used to clean out obstructions in the suction conduit using the pressurized liquid (e.g., saline) from the irrigation conduit.

The surgical system may also include a surgical gown formed from a body configured to fit on a human torso and first and second sleeves adapted to extend from a shoulder to a wrist portion. The surgical gown may include a connection system configured to attach support conduits to the surgical gown. The surgical gown, in at least one embodiment, may include support control switches that may be attached to any of the support systems.

In one embodiment, the support conduits extend from the dorsal wrist area of the surgical glove(s) along the lateral or ulnar aspect of the surgeon's arm(s), toward the shoulder, then posteriorly around the shoulder and finally caudally down the surgeon's back, where they can be directly connected to the appropriate connections. In an alternative embodiment, the support conduits may extend along medial or radial aspects of the arms, into the axilla of the shoulder, then over the lower region of the scapula and caudally down the surgeon's back. In the first embodiment, the connection system may include attachment devices on lateral aspects of the surgical gown corresponding to a forearm, upper arm, lateral shoulder, scapular, and lower lateral back areas of the surgical gown to retain support conduits extending from the surgical glove, along an arm, over a shoulder, and along a back. The attachment devices effectively, visually and physically, eliminate the independent presence of electrical wires, conduits, and other support conduits, in the surgical field. In addition, the attachment devices assist in preventing accidental entanglement or contamination of these entities without inhibiting the range of motion of a surgeon's arm or shoulder.

The invention may also be directed to a method of performing a surgical procedure in which the need to retrieve surgical implements that beforehand were rested on the surgical field is eliminated. In particular, the method may include attaching at least one surgical system to a glove worn by a person performing the surgical procedure before commencing the surgical procedure. The person conducting the surgical procedure may be, but is not limited to being, a surgeon or other appropriate person. At least one surgical instrument may be attached to the first surgical system such that the at least one surgical instrument extends proximate to a distal end of a finger of the glove to which the first surgical system is attached. The first surgical system may remain attached to the person throughout the surgical procedure eliminating need for a surgical implement assistant. For instance, the surgeon need not rest instruments on the surgical field and constantly pick up the instruments or request the instruments from an assistant. Rather, the instruments may remain attached to the surgeon throughout the duration of the surgery. Such a method enables a surgeon to work more independently and thus maintain focus on the surgical procedure.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

FIG. 11A is a volar view of a left-handed glove that can be part of a bilateral surgical system, and FIG. 11B is a dorsal view of the same left-handed glove.

DETAILED DESCRIPTION OF THE INVENTION

Figure 1:
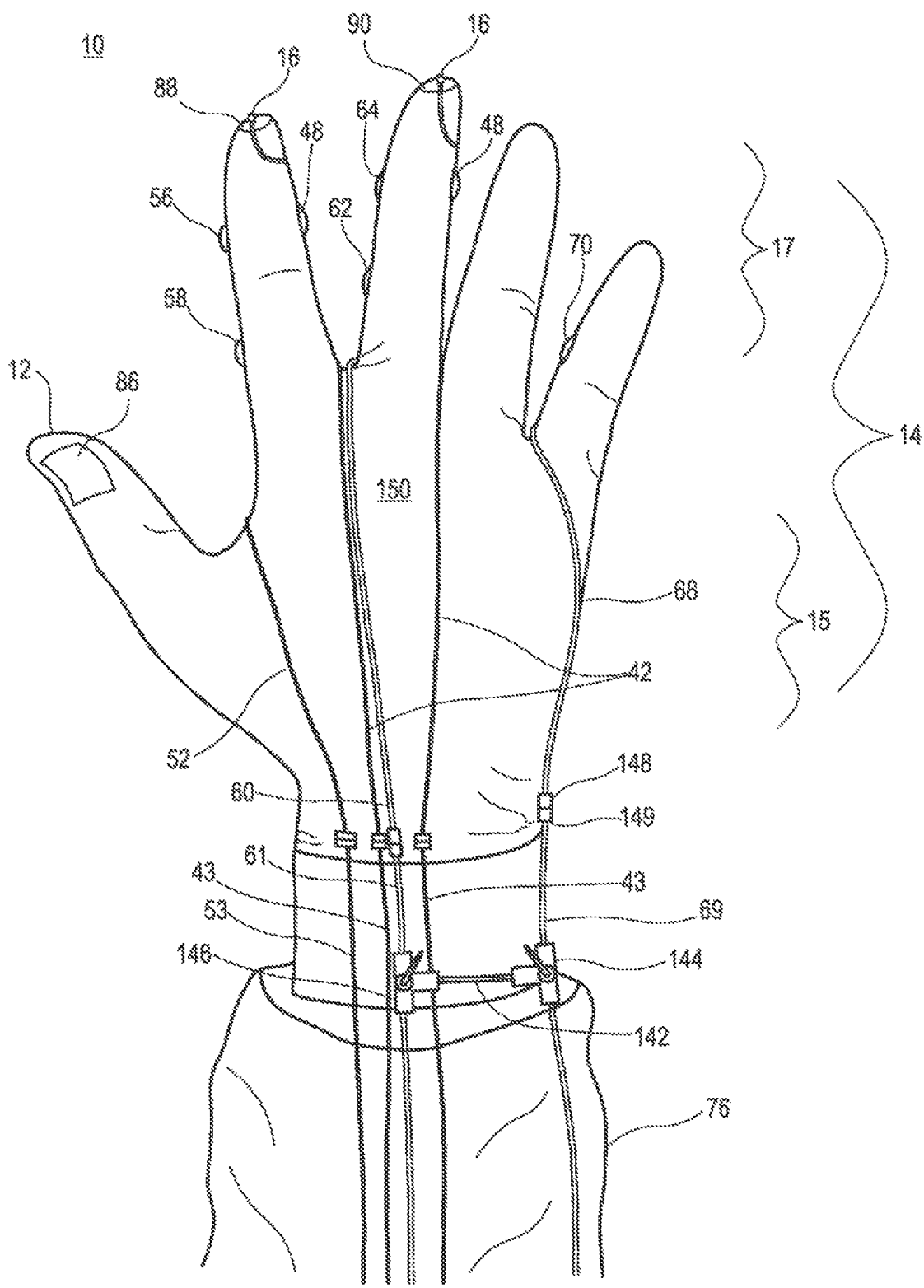
FIG. 1 is a dorsal view of a surgical system as described herein, including a right-handed glove and a shunt coupled to a sleeve of a surgical gown and a safety switch attached to a dorsal surface of the glove.

As shown in FIGS. 1-16, this invention is directed to surgical systems 10 that include one or more surgical gloves 12, 13 having support systems 14 such as, but not limited to, one or more lights 16, electrical cautery 18, suction 20 and irrigation 22. The surgical glove 12, 13 may include one or more of the lights 16, electrical cautery 18, suction 20 and irrigation 22 positioned on distal ends 24 of fingers 26 of the surgical gloves 12, 13. The support systems 14 may be controlled with switches (e.g., 48, 56, 58, 62, 64, 70 and 140) positioned on the fingers of the glove 12, 13 upon which each support system 14 is positioned. The switches may be operable with the thumb of the human hand to which the surgical glove 12, 13 is attached. The surgical system 10 may also include a surgical gown 30 having a connection system 32 for attaching support conduit 34 of the support systems 14 to the surgical gown 30. The surgical system 10 enables a surgeon to have a plurality of support systems 14 immediately available and reduces entanglement problems endemic with conventional systems.

Although the description refers to both surgical gloves 12, 13 and surgical glove 12, it should be understood that it is intended that the surgical glove 12 or gloves 12, 13 described herein can be used as part of a single glove surgical system 10 or as part of a two-glove bilateral surgical system 10, and that any surgical support system 14 attached to one glove 12, 13 could be attached to the other glove 13, 12 in a similar orientation.

As shown in the Figures, the surgical glove 12 may be configured to fit on a human hand. The surgical glove 12 may be configured to fit on a right hand or a left hand. The surgical glove 12 may be formed from any appropriate flexible and/or elastomeric material such as, but not limited to, latex and non-latex materials (e.g., nitrile, isoprene, neoprene). The surgical glove 12 may be disposable or reusable. The surgical glove 12 may also include antibacterial agents, such as a coating or other appropriate applications. The glove 12, 13 may be able to be sterilized with conventional techniques. The glove 12, 13 may be usable to be sterilized with conventional techniques.

The surgical gloves 12, 13 may include one or more support systems 14, such as, but not limited to, one or more lights 16, electrical cautery 18, suction 20 and irrigation 22. The support systems 14 may be attached to the surgical glove 12 in numerous configurations to optimize the configuration for a surgeon such that the systems 14 are located for facility of use and in a position where the systems 14 are unlikely to obstruct or conflict with the general use of the surgeon's hand or the use of surgical instruments. In at least one embodiment, the support systems 14 are integrally formed with the surgical glove 12. The support systems 14 may be nonremovably attached to the glove 12 such that the support systems 14 may remain proximate to the surgeon's hand and distal to the surgeon's wrist thereby eliminating the need for the surgeon to retrieve the implement from resting on a surgical field. In other embodiments, the support systems 14 may be removably attached to the surgical glove 12. In yet another embodiment, the support systems 14 may be positioned between layers of material forming the surgical glove 12. The support systems 14 may be attached to internal or external aspects of the surgical glove 12.

As shown in FIGS. 1-13, the surgical system 10 can include a surgical glove 12 configured to be removably attached to a human hand. The glove 12 can include first and second surgical systems 14 attached to the glove 12, wherein the first surgical system 14 comprises a first surgical instrument 17 and a first conduit 15, and the second surgical system 14 comprises a second surgical instrument 17 and a second conduit 15.

Each of the first and second surgical systems 14 can be attached to an index finger, a long finger or a little finger of the surgical glove 12. In contrast, as shown in the Figures, the thumb and the ring finger of the surgical glove 12 can be free of all surgical systems 14. The thumb and ring fingers are often used to manipulate surgical clamps during a procedure. Thus, this feature has the advantage that it allows a surgeon to wear the surgical glove through an entire procedure while leaving the thumb and ring finger free to manipulate surgical clamps.

The surgical systems 14 can also include first and second switches (e.g., 48, 56, 58, 62, 64 and 70) attached to the glove 12 for controlling the first and second surgical systems 14, respectively. The first and second switches can be attached to fingers of the glove 12 to which the first and second surgical systems 14 are attached, respectively. The first and second switches can be operable by a thumb of a human hand wearing the glove 12. The positioning of the switches (e.g., 48, 56, 58, 62, 64, 70 and 140) and surgical systems 14 can be as described herein.

The surgical systems 14 can also include (i) a safety switch 140 attached to the glove 12 for controlling the first surgical system 14 so that said first surgical system 14 will not operate unless both said first switch 28 and the safety switch 140 are actuated, or (ii) a shunt 142 for controlling fluid flow between the first and second conduits (e.g., 60 and 68). As shown in the Figures, the surgical system 14 can include one or more additional surgical systems 14 and can include both a safety switch 140 and a shunt 142.

Figure 7:
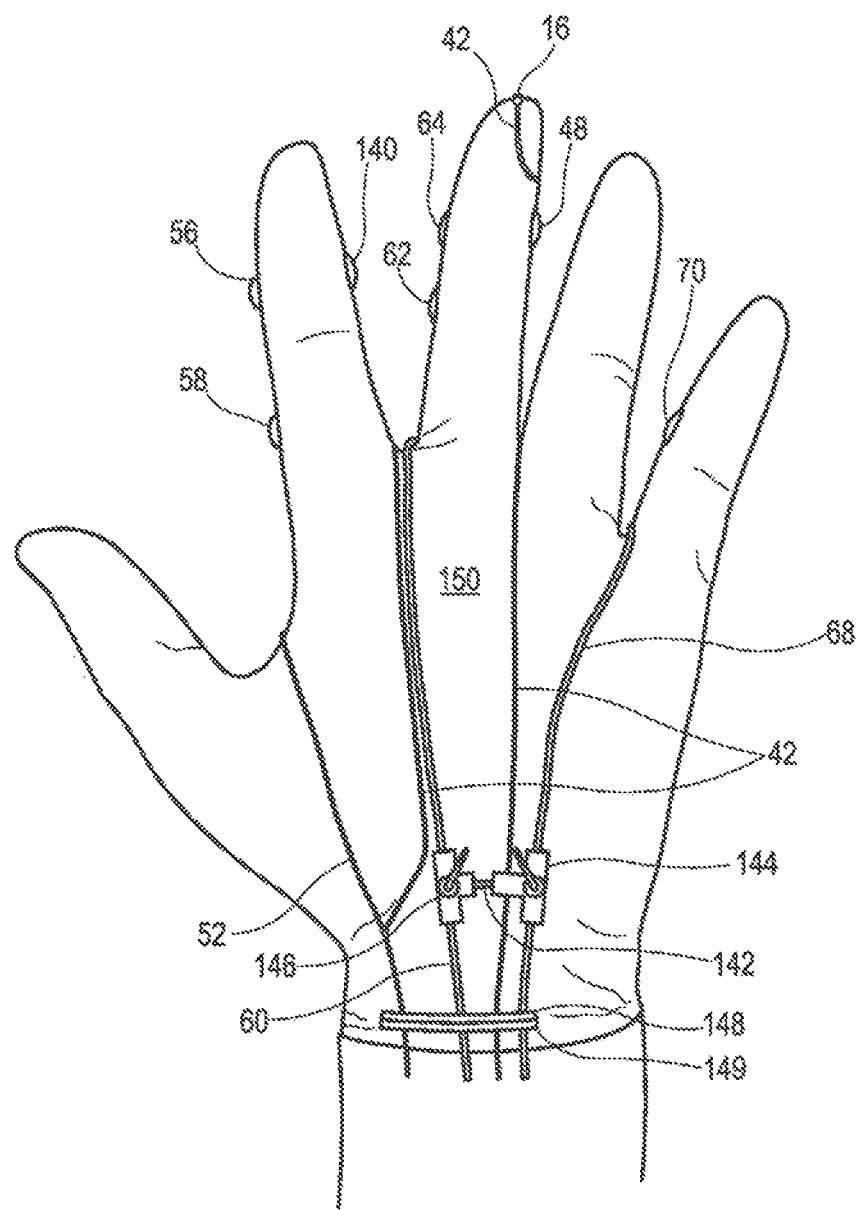
FIG. 7 is a dorsal view of a surgical system as described herein, including a right-handed glove with a shunt coupled thereto and a safety switch coupled to an ulnar surface of the index finger.
Figure 8:
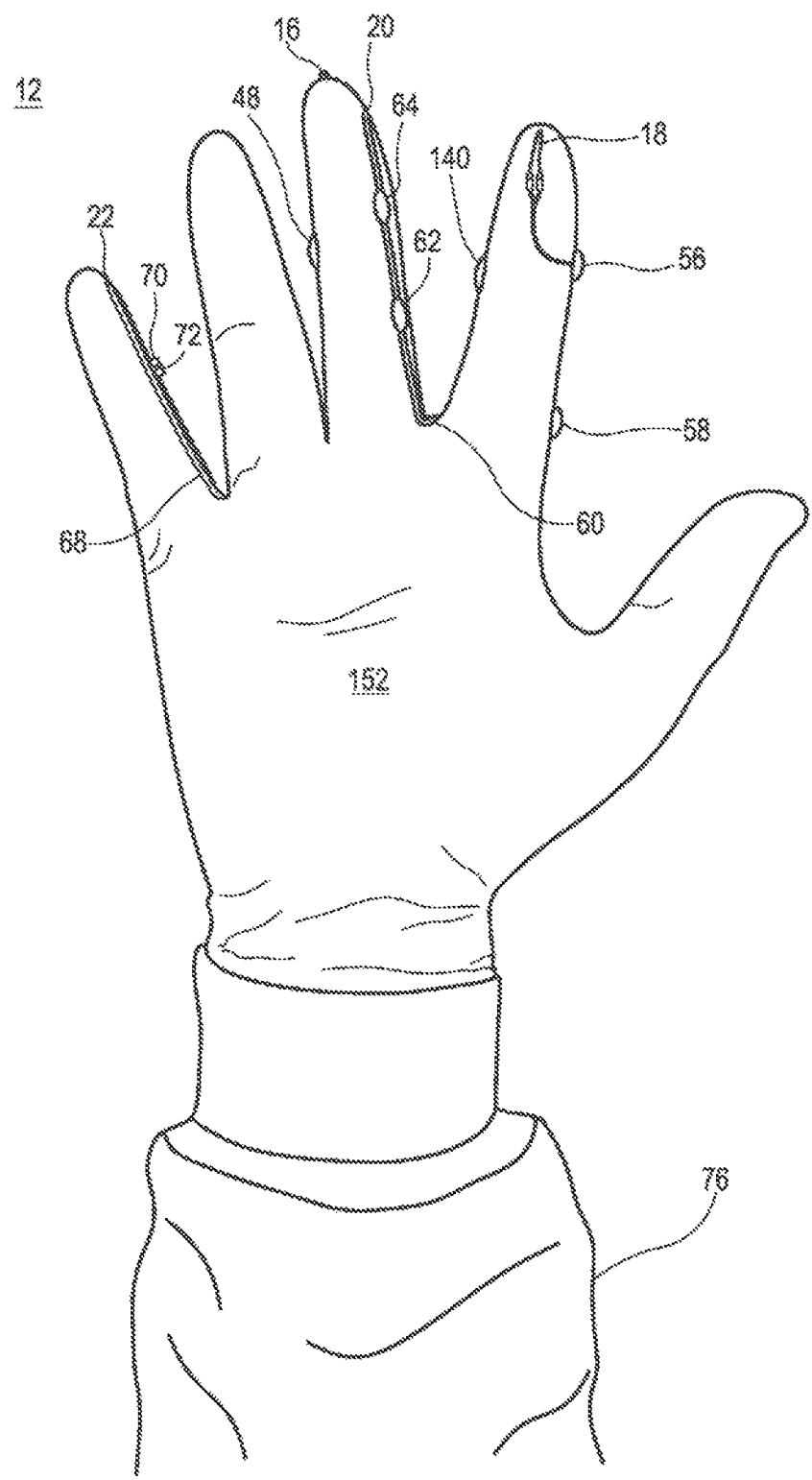
FIG. 8 is a volar view of the surgical system shown in FIG. 7.
Figure 9:
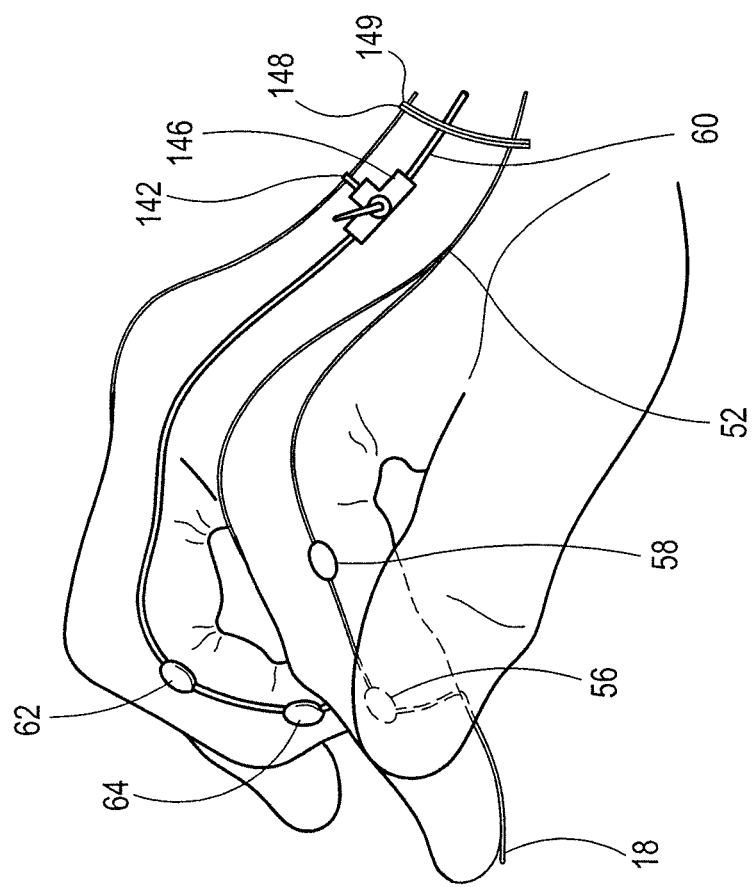
FIG. 9A is a front view and 9B a side view of the surgical glove of FIGS. 7 & 8 in which the electrical cautery is positioned to be used.
Figure 9:
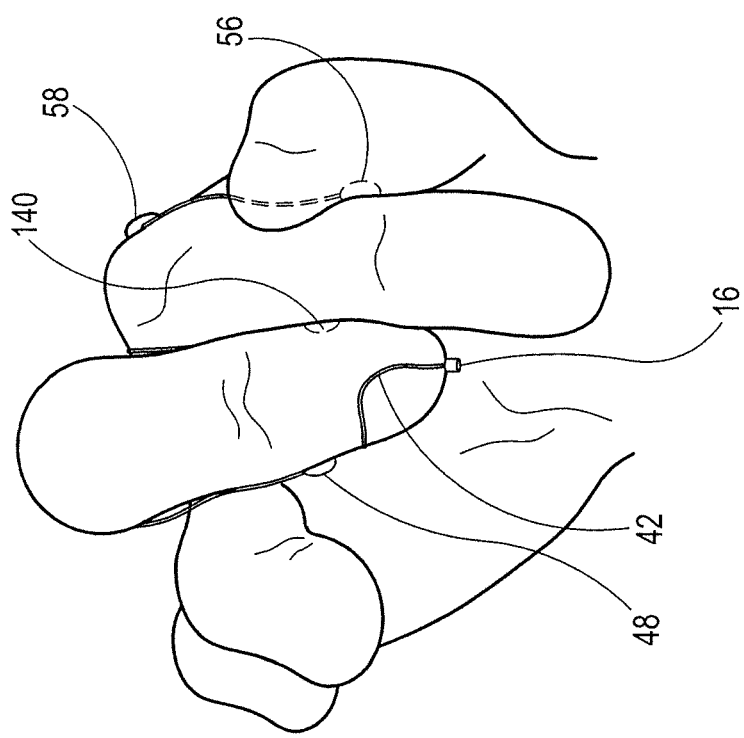

The benefits of a safety switch 140 can be particularly important in the surgical gloves 12 with integrated surgical systems 14 described herein. For example, if the cutting and cauterizing device 18 described herein accidentally fires, it can cause serious injury to the patient, the surgeon or other operating room personnel. Thus, it is important that the safety switch 140 is positioned where it is unlikely the primary control switch (e.g., 48, 56, 58, 62, 64 or 70) for the surgical system 14 and the safety switch 140 would be accidentally actuated simultaneous. FIGS. 1-4 show an exemplary glove 12 that requires two hands to actuate the cutting and cauterizing device 18; while FIGS. 7-9 show a glove 12 that requires a specific, unnatural finger positioning (see, e.g., FIGS. 9A & 9B) to actuate both the primary control switch (e.g., 56 or 58) and the safety switch (e.g., 140) simultaneously.

The shunt 142 can also be particularly important for the surgical gloves described herein. It is common for suction lines, especially smaller diameter suction lines, to become clogged during a surgical procedure. This can cause delays during a procedure or require the preparation and use of multiple suction lines during a procedure so one suction line can be used while an obstruction is being cleared from another. This is a significant problem when the suction line is integrated into the surgeon's glove. However, in the gloves described herein, the shunt 142 enables the surgeon to use the irrigation line 68, 69 to clear the obstruction in the suction line 60, 61 quickly and without removing the glove 12. Thus, the presence of the shunt 142 is a substantial improvement over prior art devices, such as those described in the Schneider Patents.

The switches (e.g., 48, 56, 58, 62, 64, 70 and 140) described herein can be appropriate switches, such as, but not limited to depression actuated switches, ports (e.g., 64), valves (e.g., in some examples, 62 and 70 can independently be valves), or other appropriate switches. The switches can be sized and positioned such that inadvertent activation by an adjacent finger or by bumping the hand on an object is unlikely.

The surgical system 10 can also include a surgical gown 30 that includes a support system comprising first and second support conduits 34 for coupling to the first and second conduits 15 of the surgical glove 12, respectively. The first and second support conduits 34 can be attached to the first sleeve 76 of the gown 30 and can terminate in support connectors 149.

The first and second surgical systems 14 can include at least one irrigation port 22 and at least one suction port 20, respectively, and the surgical system 10 can include a shunt 142 for controlling fluid flow between the irrigation conduit 68 and the suction conduit 60. The shunt 142 can be used to direct the flow of fluid from the irrigation conduit 68 to the suction line 60, 61. The shunt 142 can also be used to direct the flow of fluid toward the suction port 22, away from the suction port 22, or both, either simultaneously or alternately. As described above, this can be particularly useful for clearing debris, such as tissue, from the suction system (e.g., 22, 60 & 61) whether the debris is located upstream or downstream of the shunt.

Figure 2:
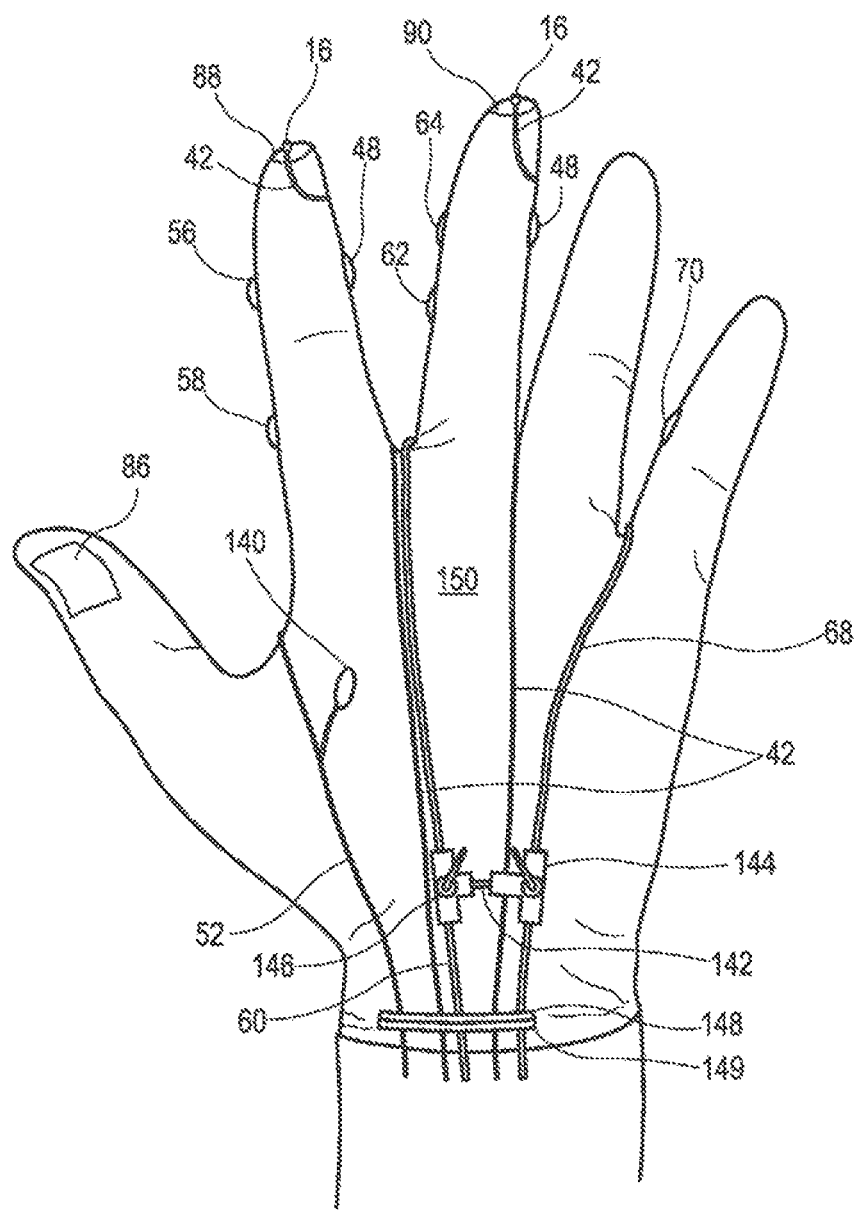
FIG. 2 is a dorsal view of a surgical system as described herein, including a right-handed glove with a shunt coupled thereto and a safety switch attached to a dorsal surface of the glove.

The shunt 142 can include first and second T-valves 144, 146 in fluid communication with the irrigation conduit 68 and the suction conduit 60, respectively. The first T-valve 144 can be in fluid communication with the second T-valve 146. As shown in FIG. 1, a first portion of the shunt (e.g., 144) can be in-line with the irrigation support conduit 69 and a second portion of the shunt (e.g., 146) can be in-line with the suction support conduit 61. Alternately, as shown in FIG. 2, a first portion of the shunt (e.g., 144) can be in-line with the irrigation conduit 68 and a second portion of the shunt (e.g., 146) can be in-line with the suction conduit 60.

As shown in FIGS. 1-4, the surgical glove 12 can include light sources 16, an electrocautery device 18, a suction port 20, and an irrigation port 22. As shown in the gloves of FIGS. 1-4, a first light source 16 can be located on a distal portion of a long finger and a light conduit 42 can run along an ulnar portion of the long finger onto a dorsal portion 150 of the metacarpals (e.g., between the third and fourth metacarpals). Similarly, a second light source 16 can be located on a distal portion of an index finger and a light conduit 42 can run along an ulnar portion of the index finger onto a dorsal portion 150 of the metacarpals (e.g., between the second and third metacarpals). The first and second light source control switches 48 can be attached to an ulnar portion of the finger of the glove to which the first and second light sources, respectively, are attached.

As shown in FIGS. 1-4 and 7-8, an electrocautery device 18 can be coupled to a distal or distal, volar 152 portion of the index finger. The electrocautery conduit 52 can run from the electrocautery device 18 along a radial portion of the index finger and then onto a dorsal portion 150 of the metacarpals (e.g., along a radial-dorsal portion of a second metacarpal). A cutting switch 56 and a coagulating switch 58 can be coupled to the electrocautery conduit 52 and positioned along a radial surface of the index finger such that the cutting and coagulating switches 56, 58 can be actuated by a thumb of the hand to which the surgical glove 12 is attached. As used herein, "electrocautery device" is used broadly and is intended to include cutting and cautery sources such as, but not limited to, electrical cautery sources, ultrasonic cutting surgical devices, and ultrasonic coagulating surgical devices.

Figure 3:
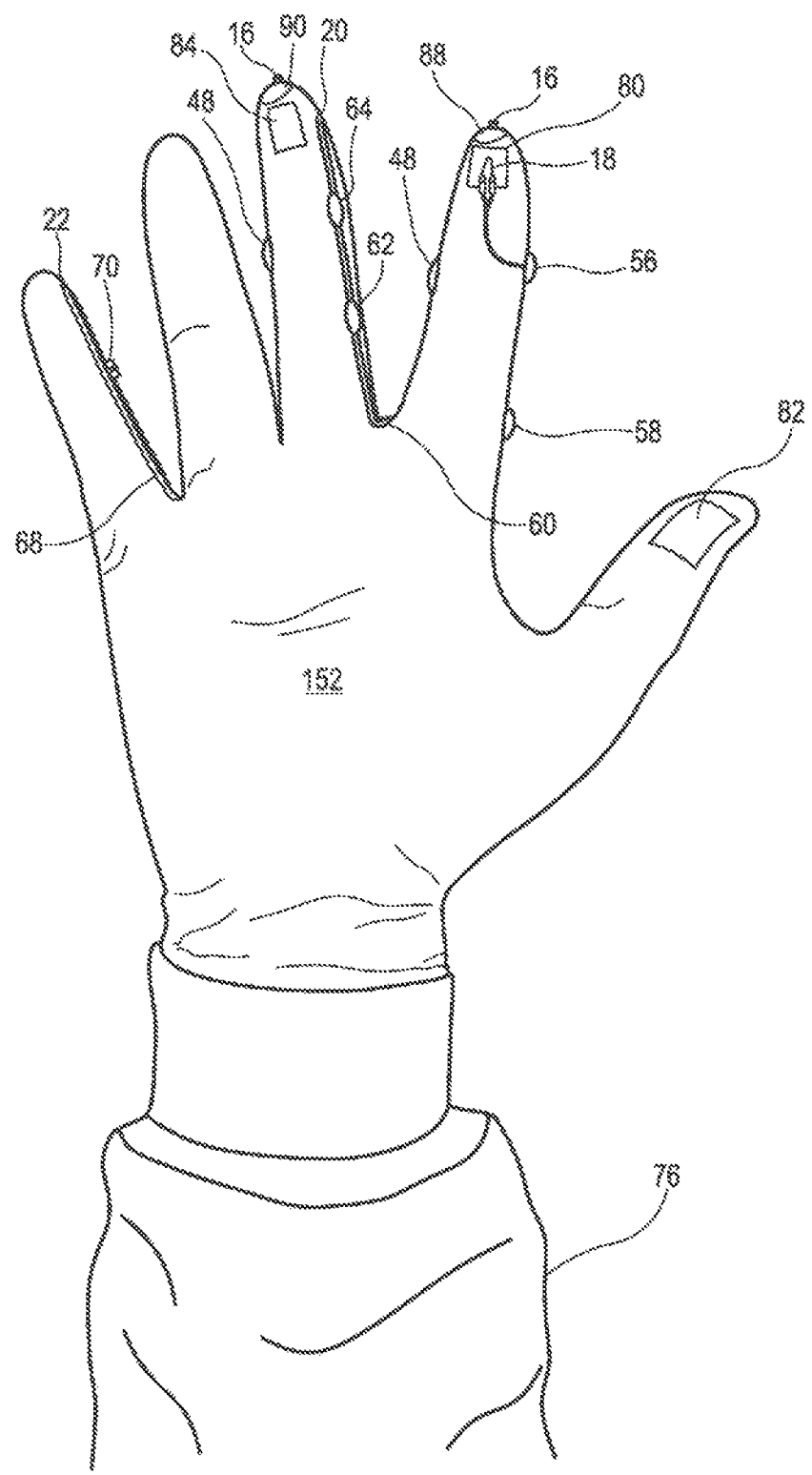
FIG. 3 is a volar view of the surgical system shown in FIGS. 1 and 2.

As shown in FIG. 3, a heat shield 80 can be coupled to the glove and positioned between the user's hand and the electrocautery tip 18. This positioning can be adapted to prevent injury to the user and/or damage to the glove. The heat shield 80 can be separate from, or coupled to, the electrocautery tip 18. The heat shield 80 can be embedded in the glove 12, 13. As will be appreciated, the heat shield 80 can be incorporated into any of the gloves 12, 13 described herein where an cutting tip 18 is utilized.

Figure 4:
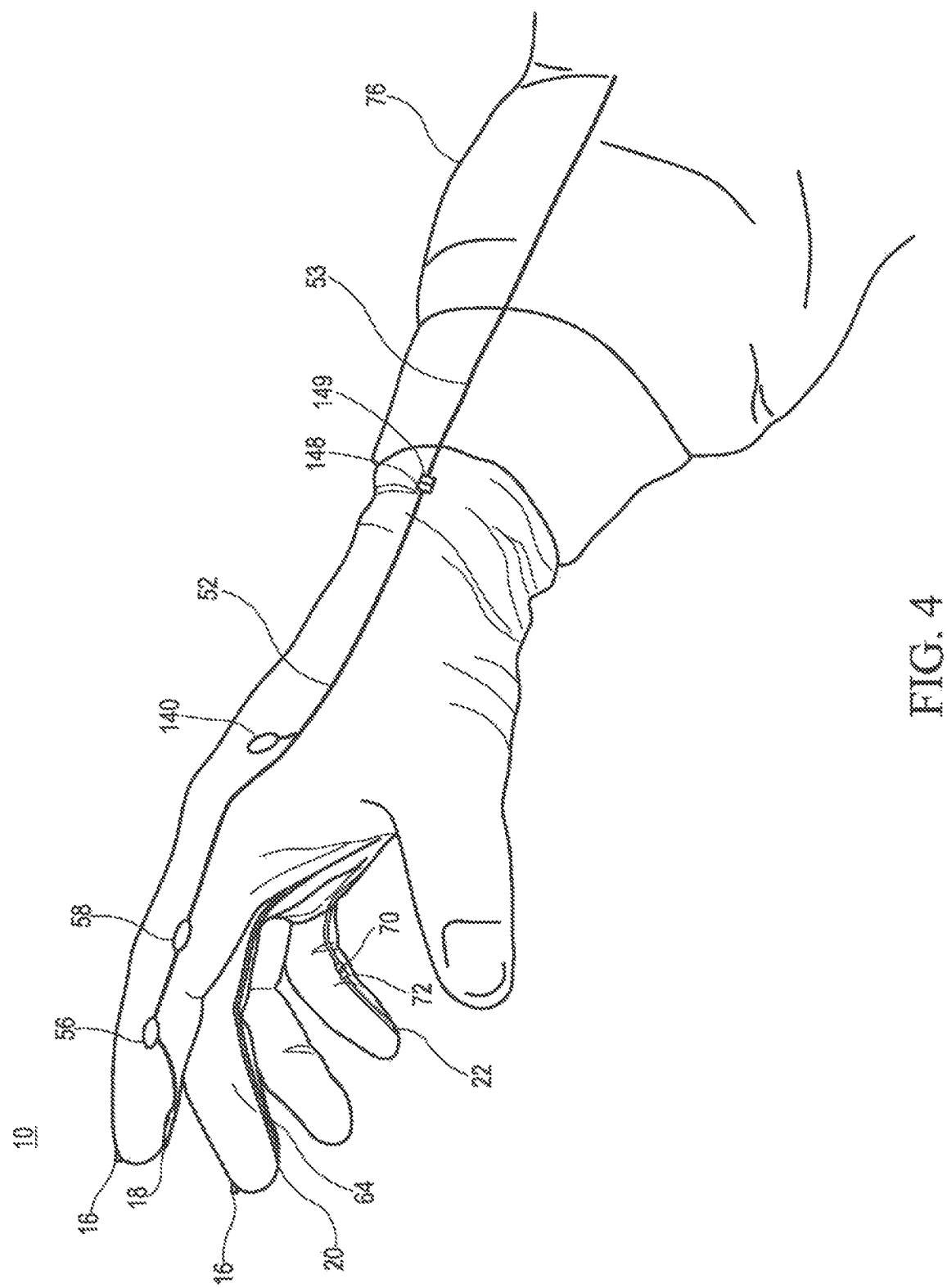
FIG. 4 is a side view of the surgical glove shown in FIG. 1.

As shown in FIGS. 1, 2 & 4, a safety switch 140 can be coupled to the electrocautery conduit 52 and positioned such that none of the fingers of the hand wearing the surgical glove 12 can actuate the safety switch 140. For example, the safety switch 140 can be positioned along a dorsal aspect 150 of the glove 12 covering the metacarpals of a hand wearing the glove. As shown in FIGS. 1, 2 & 4, the safety switch 140 can be attached to the surgical glove 12 proximate a dorso-radial aspect of a second metacarpal of a human hand wearing the surgical glove 12.

As shown in FIGS. 7-9, the safety switch 140 can be coupled to the safety branch 53 of the electrocautery conduit 52 and positioned on an ulnar aspect of the finger to which the electrocautery system 18 is coupled. In some devices, such as that shown in FIGS. 7-9, the safety switch 140 can be located on an unlar aspect of the index finger of the glove 12. For example, the safety switch 140 can be coupled to a portion of the glove that would cover an ulnar aspect of the intermediate or distal phalanx of the index finger.

The electrocautery system 18 can be designed such that the electrocautery device 18 cannot be activated unless both the safety switch 140 and the appropriate switch (56 or 58, respectively) are actuated. In the gloves of FIGS. 1, 2 & 4, the safety switch 140 will generally be actuated using the thumb of the opposing hand. Because of the positioning of the safety switch 140, activation of the electrocautery device 18 shown in FIGS. 1, 2 & 4 requires two hands, which greatly reduced or eliminates the potential for injury to the patient, the surgeon or other operating room personnel.

In contrast, FIGS. 7-9 show a glove 12 where the user can actuate the electrocautery device 18 using one hand. In particular, as shown in FIGS. 9A & 9B, one of the primary electrocautery switches 56, 58 can be actuated with the thumb (e.g., a volar aspect) and the safety switch 140 can be actuated with a radial aspect of the long finger. This configuration has the added benefit of stabilizing the index finger during cutting or coagulation procedures because the index finger is sandwiched between the thumb and the long finger when the buttons (56/58 and 140) are actuated.

As shown in FIGS. 1-4 and 7-9, a suction port 20 can be coupled to a distal or distal, radial portion of the long finger. The suction conduit 60 can run from the suction port 20 along a radial aspect of the long finger and then onto a dorsal portion 150 of the metacarpals (e.g., along a dorsal portion between the second and third metacarpals). A suction port control switch 62 and a suction control port 64 can be provided along the suction conduit 60. The suction port control switch 62 and the suction control port 64 can be positioned along a radial surface of the long finger such that the suction port control switch 62 and the suction control port 64 can be actuated by a thumb of the hand to which the surgical glove 12 is attached.

As shown in FIGS. 1-4 and 7-9, an irrigation port 22 can be coupled to a distal or distal, radial portion of the little finger. The irrigation conduit 68 can run from the irrigation port 22 along a radial portion of the little finger and then onto a dorsal portion 150 of the metacarpals (e.g., along a dorsal portion on the radial or ulnar side of the fifth metacarpal). An irrigation control switch 70 can be provided along the irrigation conduit 68. The irrigation control switch 70 can be positioned along a radial surface of the little finger such that the irrigation control switch 70 can be actuated by a thumb of the hand to which the surgical glove 12 is attached.

Figure 10B:
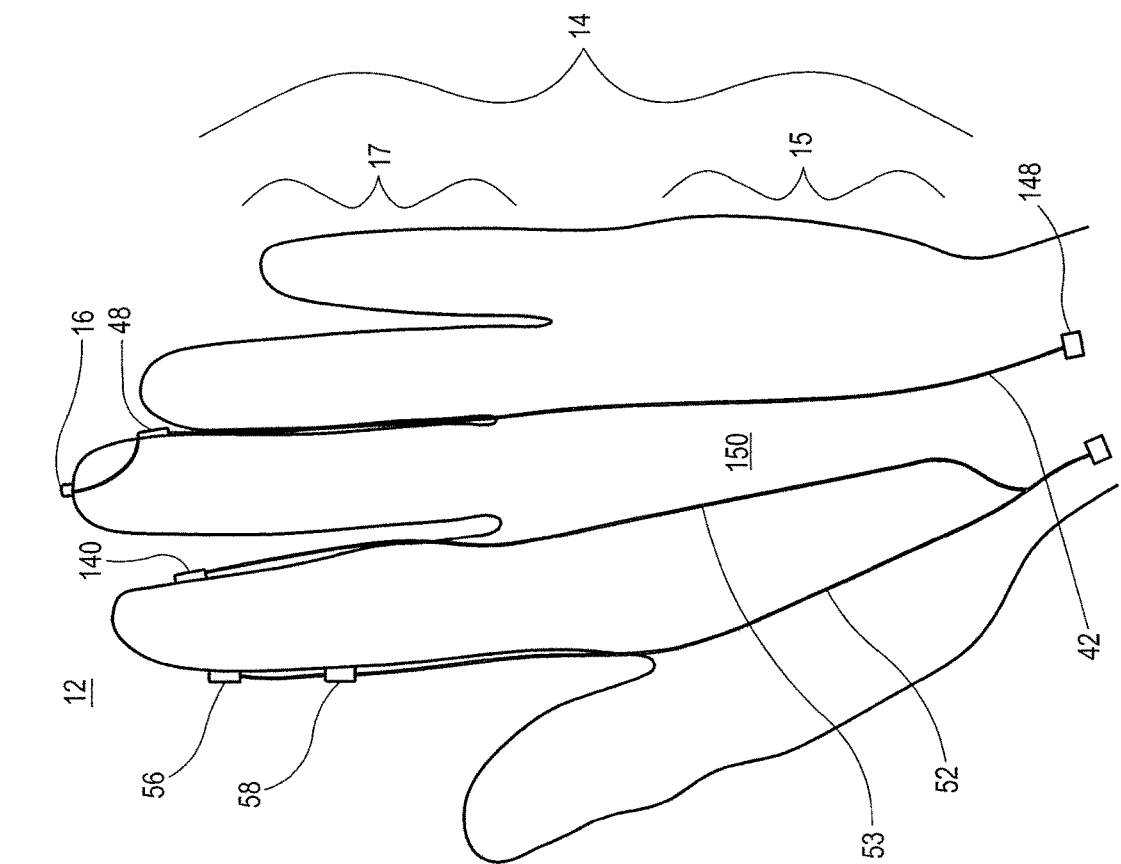
FIG. 10B is a dorsal view of the same right-handed glove.
Figure 10A:
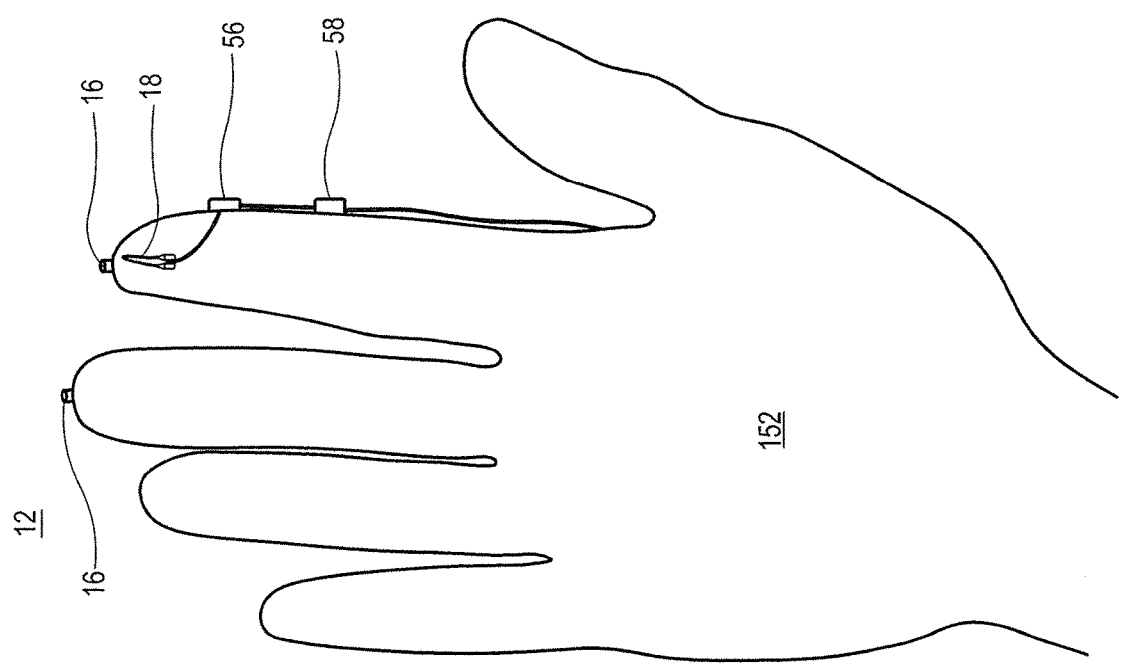
FIG. 10A is a volar view of a right-handed glove that can be part of a bilateral surgical system.

The irrigation control switch 70 may be formed from a control valve having a lever 72, as shown in FIGS. 10A & 10B, usable to turn the irrigation on and off. The lever 72 may be moved from a 3:00 position to a 6:00 position to turn irrigation on and vice versa to turn irrigation off. The irrigation control switch 70 may be sized and positioned such that inadvertent activation by an adjacent finger is unlikely. Typically, such inadvertent activation is unlikely due to the distance created between adjacent fingers by the knuckles, and the need to use the thumb to control the lever 72.

As shown in FIGS. 1-3, the surgical glove can also include additional discrete elements. The additional discrete elements can be embedded in the surgical glove. As used herein "discrete element" refers to a device or object attached to the surgical glove that does not include a conduit terminating in a terminal interconnect 148 (e.g., does not require a support conduit). Discrete elements must be adapted to support a surgical procedure in some form and do not include fillers or debris embedded within the material forming the glove. Exemplary, discrete elements include, but are not limited to, a heat shield, a reinforcing element, a battery operated light source, a reflective element, a temperature strip, and a resistance thermometer.

FIGS. 1-3 show reinforcing elements 82 and 86 on the distal volar and distal dorsal portions of the thumb, respectively. The reinforcing elements (e.g., a mesh) can be designed to prevent tears to the glove when the thumb actuates the various switches (e.g., 48, 65, 58, 62, 64 and 70) or is used to manipulate or grasp other instruments.

In addition, discrete element 84 is positioned on a distal, volar portion of the long finger. This discrete element 84 can provide a reinforcing function or can provide an independent function, such as being a resistance thermometer or a temperature strip.

Figure 6:
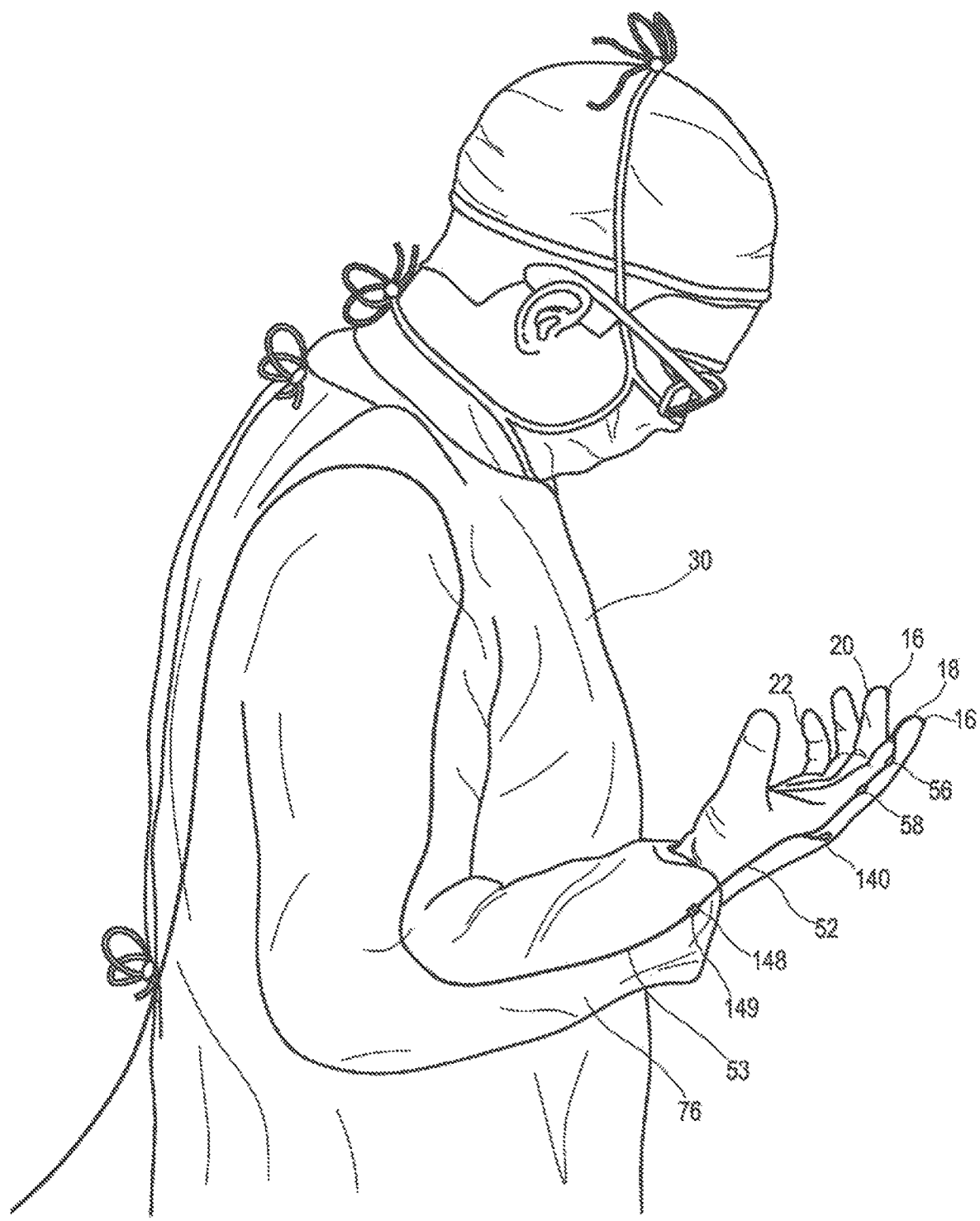
FIG. 6 is a side, perspective view of a surgeon wearing the surgical system shown in FIG. 1.

Reflective elements 88, 90 can be positioned proximate the light sources 16. As shown in FIGS. 6-8, the reflective elements 88, 90 can be positioned at distal ends of the index and long fingers, respectively. The reflective element(s) 88, 90 can be adapted for directing light emitted from the light source(s) 16 in a volar, distal direction. This enables the user to better illuminate the target, e.g., surgical field. Each reflective element 88, 90 can be separate from or coupled to the light source 16. The reflective elements 88, 90 can also be produced of a material adapted to insulate the user's hand and/or the glove from the heat radiating from the lights source 16 (e.g., halogen light).

It should be noted that, because the discrete elements (e.g., 80, 82, 84, 86, 88, 90) can be thin, uniform sheets, the discrete elements can be included on any portion of the hand or any of the fingers, including the thumb and/or ring finger, without interfering with the surgeon's ability to manipulate surgical clamps or other surgical devices while wearing the surgical gloves. Alternately, the thumb and/or ring finger of the gloves can be free of both surgical systems and discrete elements. As will be appreciated, the heat shield 80 or any other discrete element described herein can be incorporated into any of the gloves 12, 13 described herein.

Each of the conduits (42, 52, 60 and 68) can include a terminal interconnect 148 as a proximal end of the conduit. As shown in FIGS. 1 and 2, each of the terminal interconnects 148 can correspond to a support interconnect 149 located as a distal end of a corresponding support conduit (43, 53, 61 and 69). As shown in FIG. 2, the conduits (42, 52, 60 and 68) can terminate in a combined terminal interconnect 148 and the support conduits (43, 53, 61 and 69) can terminate in a combined support interconnect 149.

The terminal interconnect(s) 148 can be a male or female interconnect and the support interconnect(s) 149 can be a complementary female or male interconnect.

Each of the conduits (42, 52, 60 and 68) can traverse a mid-coronal plane of a finger of the surgical glove 12. Similarly, each of the conduits (42, 52, 60 and 68) can follow a linear isometric path along a finger of the glove. This is of great benefit as it allows the manufacture of a snug fitting surgical glove with the conduits embedded therein. In addition, it provides the surgeon with maximum dexterity while wearing the surgical system 10, which is critical for delicate surgical procedures. If, as in the prior art, the conduits are positioned along dorsal or volar surfaces of the glove, it is not possible to obtain the desired fit and dexterity without risking separation of the conduit from the glove.

In some exemplary gloves, the first and second surgical systems 14 can include at least one irrigation port 22 and at least one suction port 20, respectively, with a shunt 142 for controlling fluid flow between the irrigation conduit 68 and the suction conduit 60. Such surgical gloves can also include a third surgical system that includes a cutting source 18, an electrocautery conduit 52, and at least one of a cutting switch 56 and a coagulation switch 58. The cutting switch 56 and/or coagulation switch 58 can be attached to the same finger as the cutting source 18 and can be operable by a thumb of a human hand wearing the surgical glove. Each of the surgical devices (18, 20 & 22) can be attached to an index finger, a long finger or a little finger of the surgical glove 12.

Such a surgical glove 12 can also include a safety switch 140 for controlling the cutting source 18. The safety switch 140 can be coupled to the glove 12 or a sleeve of the gown 30 at positions as described herein. Such a surgical glove 12 can include a shunt 142 that operates as described herein and can be coupled to the conduits 60, 68 or support conduits 61, 69.

During use of the surgical system 10, a surgeon may use the various support systems 14 to assist in a surgical procedure. A surgeon may use the surgical system 10 to use the electrical cautery 18. An exemplary use of the electrical cautery device 18 of the glove in FIGS. 7 & 8 is shown in FIGS. 9A & B and described as follows. The index finger may be fully extended at the inter-phalangeal joint and flexed about 45 degrees at the metacarpal-phalangeal joint. The distal, volar aspect of the index finger may be proximate to or contacted against the surgical site. The thumb may then be opposed to the index finger. A distal, volar, ulnar aspect of the thumb may be pressed against either the cutting switch 56 or the coagulation switch 58, which are located on the radial aspect of the middle and proximal phalynx of the index finger of the surgical glove 12. The inter-phalangeal and metacarpal-phalangeal joints of the long finger can be flexed so that a radial aspect of the distal phalanx of the long finger can be pressed against the safety switch 140. The safety switch 140 can be located on the ulnar aspect of the middle phalanx. Applying pressure against the safety switch 140 and either the cutting switch 56 or the coagulation switch 58 may activate the respective function of the electrical cautery device 18. Release of pressure on either switch (i.e., 140 or 56/58) may deactivate the respective function. The remaining fingers of the hand may be held in a relaxed fashion, flexed at the metacarpal-phalangeal joint and at the inter-phalangeal joint or some other position comfortable to the user. In such an embodiment, a light source 16 from a complementary glove 13 can be used to provide illumination to a electrocautery site.

As will be apparent, similar movements of the thumb can be used to activate the surgical systems 14 with switches on radial aspects of the finger to which they are attached. In FIG. 1, additional exemplary surgical system switches positioned on radial aspects of a finger include the irrigation switch 70 and the suction switches 62, 64.

Figure 5:
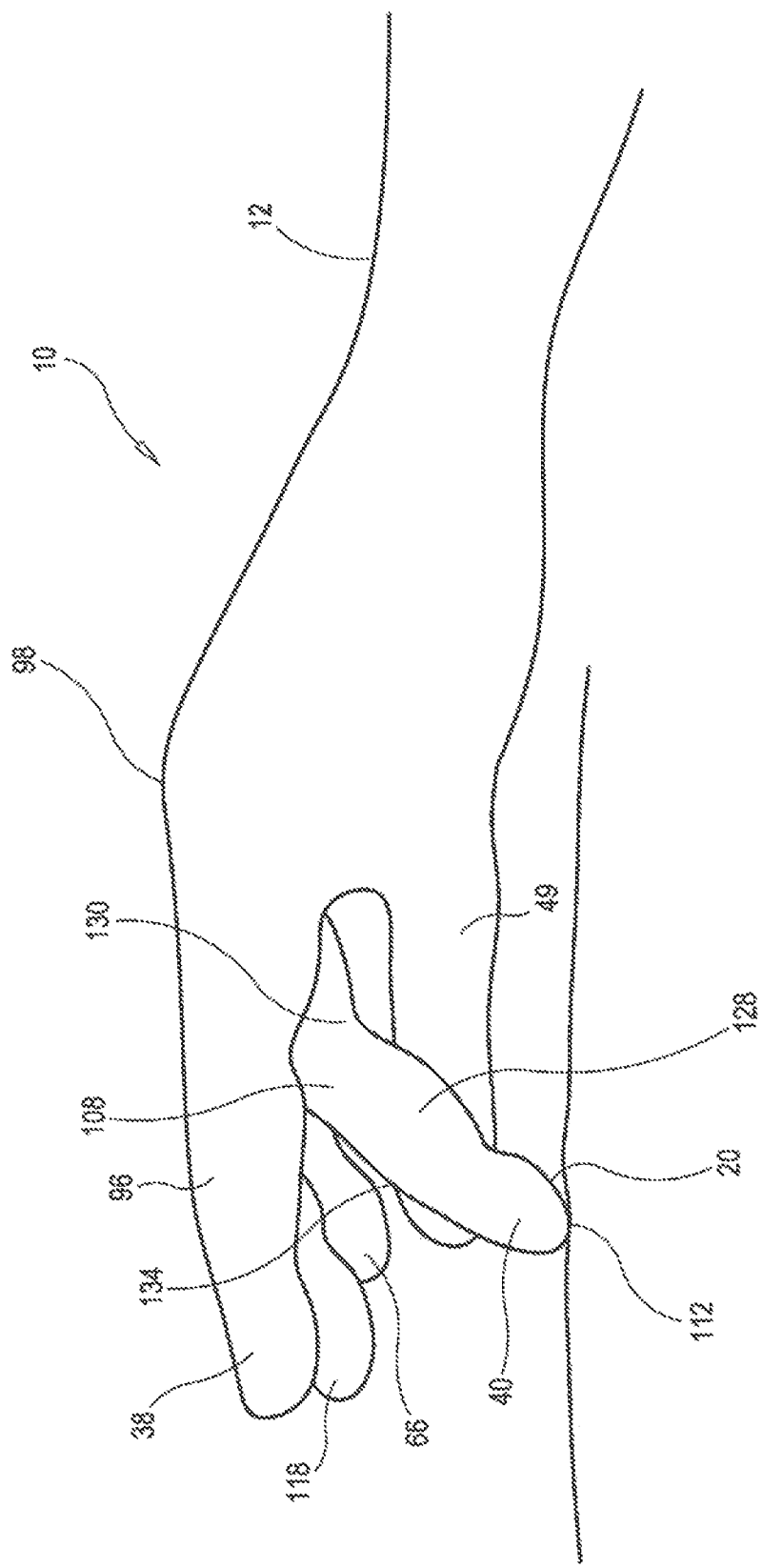
FIG. 5 is a side view of a hand positioned to actuate the light source switch positioned on an ulnar surface of the long finger.

The light source control switch 48 can be positioned on an ulnar aspect of a finger to which the light source 16 is attached. As shown in FIG. 5, the light source control switch 48 can be used by bending the long finger 40 at the proximal inter-phalangeal joint 130 while extending the long finger 40 at the distal inter-phalangeal joint 128. The distal, dorsal-ulnar aspect of the thumb 49 may then be opposed to the ulnar aspect of the middle phalanx 134 of the long finger 40 and pressed against the light source control switch 48. The switch 48 may be configured such that application of pressure by the thumb 49 causes the light source 16 to be turned on. Application of pressure by the thumb 49 may also turn the light source 16 off. Once activated, the light source 16 can provide illumination to a designated location by pointing the finger 38, 40 toward an area of interest. The same process may be used for light source control switches positioned on the index finger 38.

Figure 14:
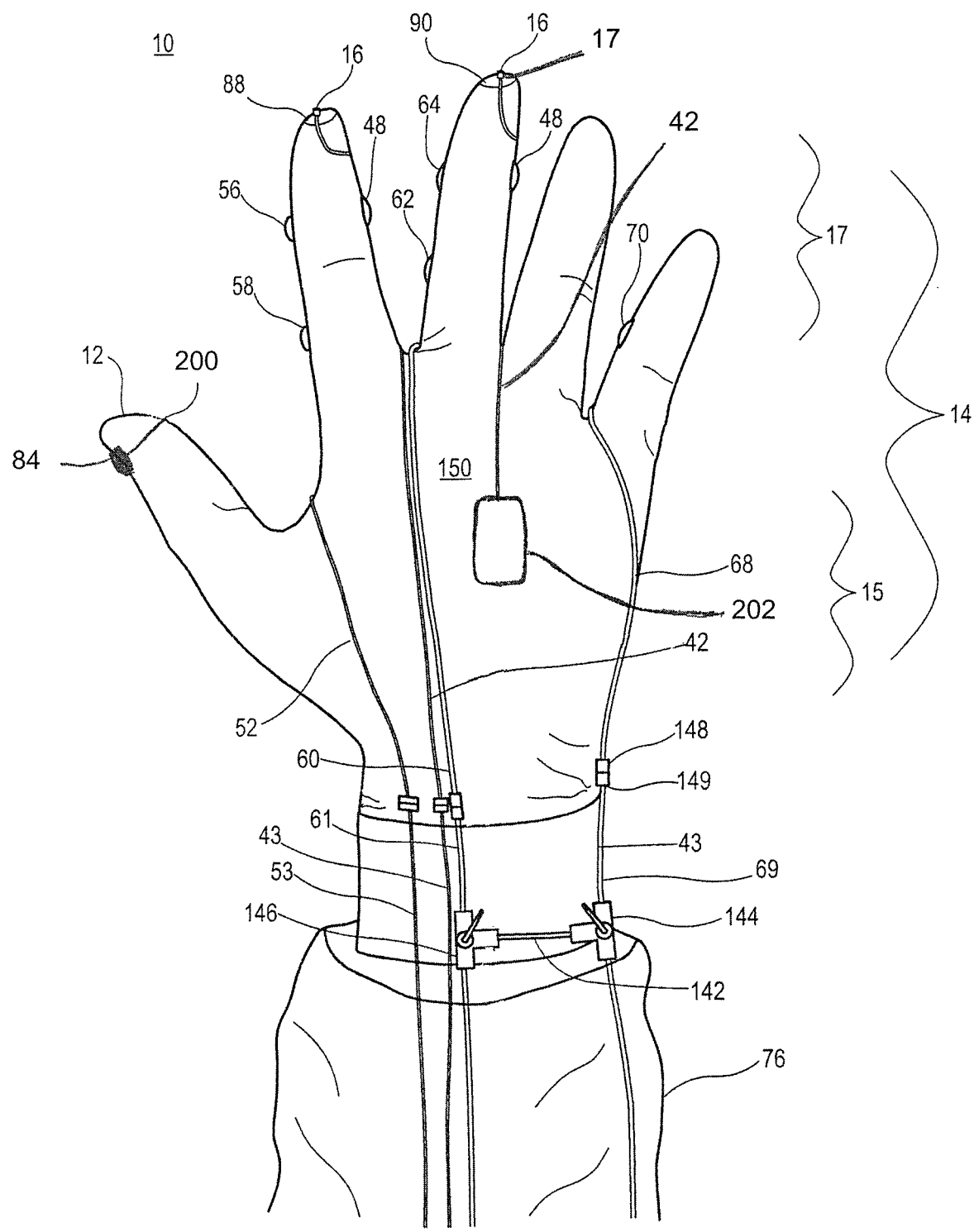
FIG. 14 is a dorsal view of a surgical system as described herein, including a right-handed glove and a surgical instrument that is operated by a discrete element located on a dorsal aspect of the thumb of the glove.
Figure 15:
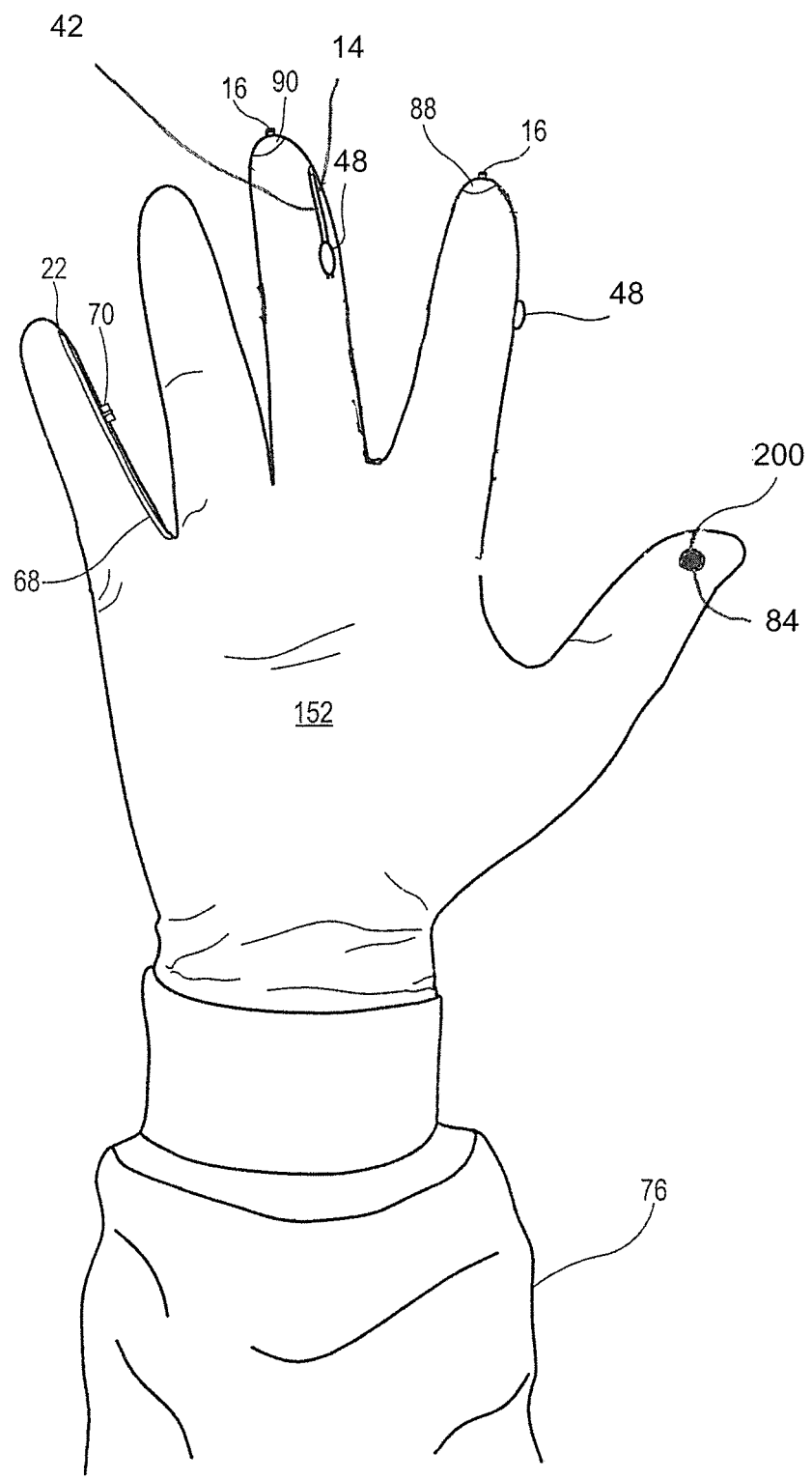
FIG. 15 is a volar view of a variation of the surgical glove of FIG. 14, where the discrete element is located on a volar surface of the thumb of the glove.
Figure 16:
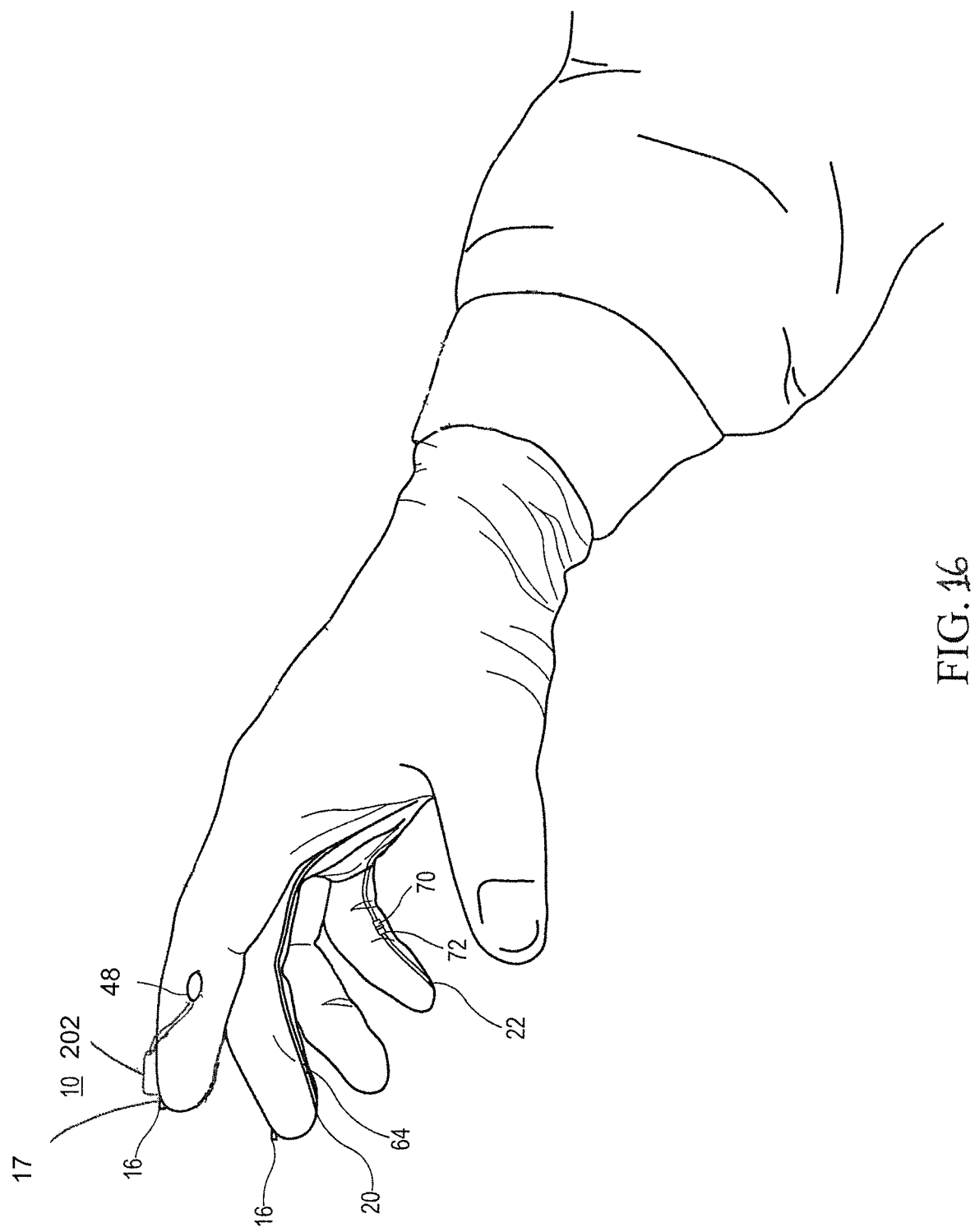
FIG. 16 is a side view of the surgical glove shown in FIG. 15.

FIGS. 14-16 show embodiments of the surgical system that include a surgical glove with a first switch 48 that is actuated due to the proximity of an actuating element 200, which can be a discrete element 84. In such embodiments, the switch 48 can be a static switch (e.g., a proximity switch). In other words, there are no externally actuated buttons or switches involved with the actuation mechanism. For example, the switch 48 can be a reed switch, which is actuated by placing a magnet in close proximity to the switch. While a magnetic field is one example of a proximity switch, the mechanism of the static switch can rely on other electromagnetic fields. It will also be understood that any of the switches (48, 56, 58, etc.) described herein can be static switches (e.g., proximity switches) or other conventional switches (e.g., toggle switches, pushbutton switches, pressure switches, etc.)

The proximity switch can be a latching switch or a non-latching switch. A latching switch will switch-on and stay on once it is actuated by the actuating element 200 even after the actuating element 200 is removed from the general vicinity of the switch. The latching switch will switch-off when the actuating element 200 is again brought close enough to the switch to release the latch. A non-latching proximity switch will remain on when the actuating element 200 is adjacent the switch, but will turn off when the actuating element 200 is no longer proximate to the switch.

As shown in FIGS. 14-16, in some embodiments, the surgical system 10 can include a surgical glove 12 configured to be removably attached to a human hand. The surgical glove 12 can include a first surgical instrument 17 attached to the surgical glove 12, where the first surgical instrument 17 is nonremoveably, integrally attached to the surgical glove 12 during the formation of the surgical glove 12, and the first surgical instrument 17 is coupled to a finger of the surgical glove. In some embodiments, as shown in FIGS. 14-16, the surgical glove 12 can also include a first switch 48 attached to the surgical glove for controlling the first surgical support system 17, and a first actuating element 200 attached to a thumb of the surgical glove 12. The first actuating element 200 can be a discrete element. In some embodiments, the first switch 48 is actuated when the first actuating element 200 is placed in close proximity to the first switch 48, and a thumb of the surgical glove is free of surgical support systems.

In some embodiment, the first surgical support system 17 can be a light source 16. In some embodiments, as shown in FIGS. 14-16, the first surgical instrument 17 can include an LED light source. In some embodiments, as shown in FIG. 16, the first surgical instrument 17 is a discrete element.

In some embodiments, the first actuating element 200, the first switch 48, or both comprise a magnet. In some embodiments, the first actuating element 200 comprises a magnet.

In some embodiments, as seen in FIGS. 14 & 16, the first surgical instrument 17 is operatively connected to a power source 202. In some embodiments, the power source 202 includes a battery. In some embodiments, as evident from FIG. 16, the surgical instrument 17 (e.g., light source) and the power source 202 can be integrated into a single housing. In other embodiments, as shown in FIG. 14, the surgical instrument 17 and the power source 202 can be connected by a conduit 42.

In some embodiments, the first actuating element 200 is located on the thumb of the glove 12. In some embodiments, as shown in FIGS. 14 and 15, the first actuating element 200 is located on a distal aspect of the thumb of the glove 12. In some embodiments, the first actuating element 200 is located on a distal volar aspect of the thumb of the glove 12, a distal dorsal aspect of the thumb of the glove 12, a distal-radial aspect of the thumb of the glove 12, or a distal-ulnar aspect of the thumb of the glove 12.

In some embodiments, a first conduit 42 is operatively connected to the first surgical instrument 17, where the first conduit 42 is coupled to a finger of the surgical glove 12. In some embodiments, as best seen in FIG. 14, the first conduit 42 is operatively connected to a power supply 202 (e.g., battery) to supply power to the first surgical instrument 17/16.

In some embodiments, the first surgical instrument 17 comprises an instrument selected from the group consisting of at least one at least one electrical cautery source, at least one ultrasonic cutting surgical device, at least one ultrasonic coagulating surgical device, at least one light source, at least one irrigation port, and at least one suction port. In some embodiments, the first surgical instrument 17 is coupled to an index finger, a long finger, or a little finger of the surgical glove 12.

In some embodiments, the surgical system comprising a proximity switch (e.g., a reed switch) can be used while performing a surgical procedure. In such embodiments, the method of performing a surgical procedure can include providing a surgical system comprising a proximity switch to control at least one surgical instrument, attaching the surgical glove to a person conducting a surgical procedure (e.g., donning the glove); and actuating the first surgical instrument using the first actuating element as part of the surgical procedure performed by the person.

Although FIGS. 1-9 and 14-16 are depicted with respect to a right-handed glove, it should be understood that any of the descriptions provided herein can apply equally to left-handed gloves. To facilitate the description of left-handed gloves, the positioning of all aspects of the surgical system have been provided such that they are unambiguous regardless of whether they refer to a right-handed glove or a left-handed glove. Of course, any and all of the surgical systems described herein can be attached to a right-handed glove or a left-handed glove. In some instances, the surgical system can include both a right-handed glove and a left-handed glove.

Bilateral Surgical System

As shown in FIGS. 10A, 10B, 11A & 11B, a bilateral surgical system that includes primary and complementary gloves 12, 13 configured to be removably attached to a pair of human hands is also described. FIG. 10 shows the volar (FIG. 10A) and dorsal (FIG. 10B) views of an exemplary right-handed surgical glove. FIG. 11 shows the volar (FIG. 11A) and dorsal (FIG. 11B) views of an exemplary left-handed surgical glove 13. Although not shown in FIGS. 10A, 10B, 11A & 11B, it will be understood that discrete elements 80, 82, 84, 86, 88, 90 can be incorporated into the gloves 12, 13 of the bilateral system in the same manner and positions as are described above with respect to FIGS. 1-3.

The surgical glove system disclosed in the Schneider Patents is a unilateral, single hand system, which requires support system activation by the same hand's thumb. Thus, gloves from the Schneider Patents do not allow for the simultaneous use of more than one of integral surgical support systems. This means that simultaneous use of suction with electrical cautery, suction with irrigation, or spot illumination with either electrical cautery, suction or irrigation is cannot occur without assistance from another member of the surgical team—likely using conventional handheld devices. The novel bilateral devices described herein provide efficient, user-friendly systems that eliminate entanglement reliably, and allow for simultaneous use and activation of more than one integral surgical support system. Thus, the bilateral systems described herein are a substantial improvement over the unilateral systems described in the Schneider Patents, which help address some problems of the prior art without fully overcoming them.

It should be noted that the terms "primary" and "complementary" are used broadly to avoid confusion regarding the positioning of surgical systems attached to the gloves. Thus, except where otherwise specified, both the "primary" and "complementary" gloves can be designed for either the dominant hand or the non-dominant hand of the user.

As shown in FIGS. 10A & 10B, the primary glove 12 can include a first surgical system 14 coupled to a finger of the primary glove 12. The first surgical system 14 can include a first surgical instrument 17, a first conduit 15 coupled to the primary glove, and a first switch (e.g., 48, 56, 58) coupled to the primary glove 12. The first switch (e.g., 48, 56, 58) can be for controlling the first surgical system 14 and can be coupled to a finger of the primary glove 12 to which the first surgical system 14 is coupled.

As shown in FIGS. 11A & 11B, the complementary glove 13 can include a second surgical system 14 coupled to a finger of the complementary glove 13. The second surgical system 14 can include a second surgical instrument 17, a second conduit 15 coupled to the complementary glove 13, and a second switch (e.g., 48, 62, 64, 70) coupled to the complementary glove 13. The second switch (e.g., 48, 62, 64, 70) can be for controlling the second surgical system 14 and can be coupled to a finger of the complementary glove 13 to which the second surgical system 14 is coupled. The first and second surgical systems 14 can be different.

As shown in FIGS. 10A, 10B, 11A & 11B, the first surgical system 14 can be coupled to an index finger, a long finger or a little finger of the primary glove 12, and the second surgical system 14 can be coupled to an index finger, a long finger or a little finger of the complementary glove 13. The first and second conduits 15 can traverse a mid-coronal plane of a finger of the glove 12, 13 to which the first and second conduits 15 are coupled. The thumb and ring finger of the primary glove 12, the complementary glove 13, or both, can be free of surgical systems 14.

As shown in FIGS. 10A & 10B, the bilateral surgical system can also include a third surgical system 14 coupled to the primary glove 12. The third surgical system 14 can include a third surgical instrument 17, a third conduit 15 coupled to the primary glove 12, and a third switch (e.g., 48, 56, 58) coupled to the primary glove 12 for controlling the third surgical system 14. The third surgical systems 14 can be coupled to an index finger, a long finger or a little finger of the primary glove 12 and the third switch (e.g., 48, 56, 58) can be coupled to a finger of the primary glove 12 to which the third surgical system 14 is coupled.

In bilateral surgical systems, such as that shown in FIGS. 10A, 10B, 11A & 11B, the first surgical system 14 can include a cutting device 18 selected from at least one electrical cautery source, at least one ultrasonic cutting surgical device, at least one ultrasonic coagulating surgical device or a combination thereof. The second surgical system 14 can include at least one light source 16, at least one irrigation port 22, or at least one suction port 20, and the third surgical system 14 can include at least one light source 16.

Figure 12:
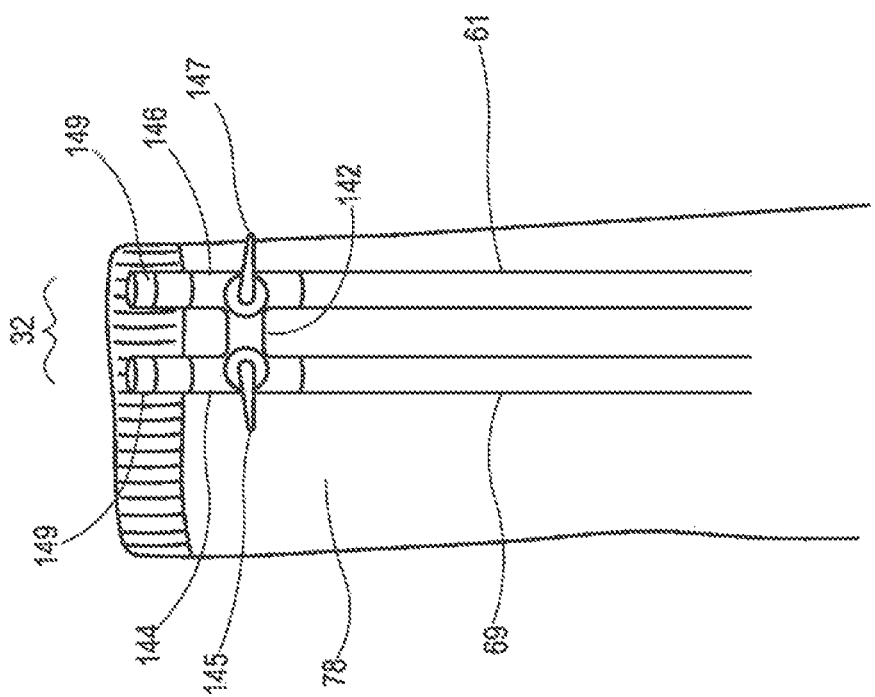
FIG. 12 is a dorsal view of a shunt coupled to the left sleeve of a surgical gown for use in connection with the left-handed glove of FIGS. 11A & 11B.

As shown in FIGS. 11A & 11B, the second and fourth surgical systems 14 can comprise at least one irrigation port 22 and at least one suction port 20, respectively. A shunt 142 connecting the second conduit 68 and the fourth conduit 60 can be present either coupled to the glove 12, 13, as in FIG. 2, or coupled to the sleeve of a surgical gown, as shown in FIGS. 1 & 12. Consistent with the shunts 142 described herein, the shunt 142 can be adapted for diverting the flow of liquid from the second conduit 68 to the fourth conduit 60. The shunt 142 can direct the flow of liquid through the fourth conduit 60 toward the fourth surgical instrument 20, away from the fourth surgical instrument 20, or both, either simultaneously or alternately. This has the benefit that it allows the surgeon to clear an obstruction from the suction conduit 60 or suction support conduit 61 without removing the glove 13 and without using an external device (e.g., a brush or syringe) as is the common practice when using conventional suction lines. This is critical to avoiding significant delays because the surgeon needs to change gloves during a procedure or physically clear the debris.

The shunt 142 can also include first and second T-valves 144, 146 in fluid communication with the irrigation conduit 68 and suction conduit 60, respectively. The first T-valve 144 can be in fluid communication with the second T-valve 146. Each of the T-valves 144, 146 can include a three-way stopcock valve 145, 147. As shown in FIGS. 1 & 12, a first portion of the shunt (e.g., 144) can be in-line with the irrigation support conduit 69 and a second portion of the shunt (e.g., 146) can be in-line with the suction support conduit 61. Alternately, as shown in FIG. 2, a first portion of the shunt (e.g., 144) can be in-line with the irrigation conduit 68 and a second portion of the shunt (e.g., 146) can be in-line with the suction conduit 60.

In some bilateral surgical system, the complementary glove 13 can include a fourth surgical system 14. The fourth surgical system 14 can include a fourth surgical instrument 17, a fourth conduit 15 coupled to a finger of the complementary glove 13, and a switch (e.g., 48, 62, 64, 70) for controlling the fourth surgical system 14. The fourth switch (e.g., 48, 62, 64, 70) can be coupled to a finger of the complementary glove 13 to which the fourth surgical system 14 is coupled. The thumb and ring finger of the complementary glove 13 can be free of surgical systems 14.

In such bilateral surgical systems, as shown in FIGS. 10A & 10B, the primary glove 12 can include a first surgical system 14, such as a cutting source 18 selected from at least one electrical cautery source, at least one ultrasonic cutting surgical device, and at least one ultrasonic coagulating surgical device; and a third surgical system 14, such as at least one light source 16. As shown in FIGS. 11A & 11B, the complimentary glove 13 can include a second surgical system 14, such as at least one light source 16, at least one irrigation port 22, or at least one suction port 20; a fourth surgical system 14, such as at least one light source 16, at least one irrigation port 22, or at least one suction port 20; and a fifth surgical system 14, such as at least one light source 16.

In such surgical systems, the second and fourth surgical systems 14 can provide different functions. For example, the second and fourth surgical systems can include at least one irrigation port 22 and at least one suction port 20, respectively. As shown in FIG. 2, a shunt 142 can be positioned to controllably connect the second conduit (e.g., 68) and the fourth conduit (e.g., 60) or, as shown in FIGS. 1 & 12, the shunt 142 can be positioned to controllably connect a second support conduit (e.g., 69) and a fourth support conduit (e.g., 61).

Figure 13:
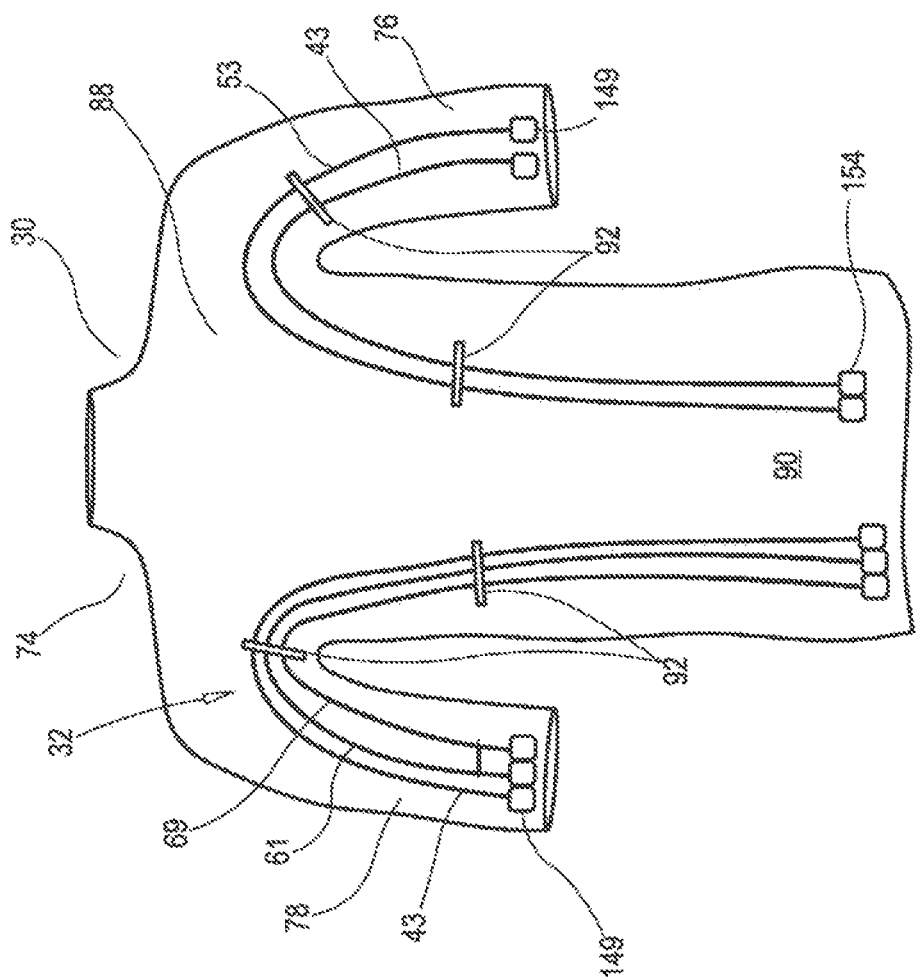
FIG. 13 is a rear view of a surgical gown for use in connection with a bilateral surgical system.

As shown in FIG. 13, any of the bilateral surgical systems described herein can also include a surgical gown 30 formed from a body 74 adapted to fit onto a torso of a human, first and second sleeves 76, 78 extending from the body 74 and sized to extend from a shoulder of a human to a wrist of a human. The gown 30 can include a support system 32 comprising first and second support conduits 34 for coupling to the first and second conduits 15, respectively. The first and second support conduits 34 can be attached to first and second sleeves of the gown 76, 78, respectively. The surgical gown 30 can include attachment devices 92 on lateral aspects of forearm, upper arm, lateral shoulder, scapular, and lower lateral back areas of the surgical gown 30 to retain the support conduits 34 extending from the primary and complementary gloves 12, 13, along an arm of a human, over a shoulder of the human, and along a back of the human.

Each and every one of the surgical systems 14 can be attached to an index finger, a long finger or a little finger of the surgical gloves 12, 13. Similarly, as shown in the Figures, the thumb and the ring finger of the surgical gloves 12, 13 can be free of all surgical systems 14.

As shown in FIGS. 10A, 10B, 11A & 11B, the surgical glove 12 can include a cutting system that includes a cutting device 18, such as an electrocautery device, coupled to a distal, volar portion of an index finger. The electrocautery device 18 is coupled to an electrocuatery conduit 52, which is coupled to a cutting switch 56, a coagulation switch 58, and a safety switch 140. The electrocautery conduit 52 runs from the electrocautery device 18 along the radial aspect of the index finger and then onto a dorsal surface 150 of the metacarpals. The cutting switch 56 and coagulation switch 58 can be located along radial portions of the index finger. The electrocautery conduit 52 also includes a safety branch 53 for the safety switch 140. The safety branch 53 of the electrocautery conduit 52 can extend between the second and third metacarpals and then along a dorsal or dorsal, volar aspect of the index finger. The safety switch 140 can be positioned along a dorsal aspect of the index finger proximate an intermediate or distal phalanx. The electrocautery conduit 52 can run along a dorsal-radial aspect of the second metacarpal and end in a terminal connection 148.

Alternately, as shown in FIG. 1, the safety switch 140 can be positioned along a dorsal aspect of the second metacarpal. For example, along a radial, dorsal aspect of the second metacarpal.

As shown in FIGS. 10A & 10B, the surgical glove 12 can include at least one light source 16. Each of the light sources 16 can be coupled to a light source conduit 42 and a light source control switch 48. The light source(s) 16 can be coupled to a distal or distal, dorsal aspect of the index finger and/or long finger. The light source control switch 48 can be located along an ulnar aspect of the index finger and/or long finger. The first light source conduit 42 can run from the light source 16 along an ulnar aspect of the long finger and then onto a dorsal surface 150 of the metacarpals (e.g., a dorsal-ulnar aspect of the third metacarpal) and end in a terminal connection 148. Where applicable, the second light source conduit 42 can run from the light source 16 along an ulnar aspect of the index finger and then onto a dorsal surface 150 of the metacarpals (e.g., a dorsal-ulnar aspect of the second metacarpal) and end in a terminal connection 148. Generally, the second light source 16 is reserved for embodiments, such as FIGS. 1-3, where the safety switch 140 is not located on the index finger.

As shown in FIGS. 11A & 11B, the surgical glove 13 can include an irrigation system that includes an irrigation port 22 coupled to a distal or distal, volar portion of a little finger of the surgical glove 13. The irrigation port 22 can be coupled to an irrigation conduit 68 that is coupled to an irrigation control switch 70. The irrigation conduit 68 can run from the irrigation port 22 along the radial aspect of the little finger and then onto a dorsal surface 150 of the metacarpals. The irrigation control switch 70 can be coupled to a radial aspect of the little finger. The irrigation conduit 22 can run along a dorsal-radial or dorsal-ulnar aspect of the fifth metacarpal and end in a terminal connection 148.

The surgical glove 13 can include a suction system 20 that includes a suction port 20, coupled to a distal or distal, volar portion of a long finger of the surgical glove 13. The suction port 20 can be coupled to a suction conduit 60 that is coupled to a suction port control switch 62 and a suction control port 64. The suction conduit 60 can run from the suction port 20 along the radial aspect of the long finger and then onto a dorsal surface 150 of the metacarpals. The suction port control switch 62 and the suction control port 64 can both be coupled to a radial aspect of the long finger. In particular, the suction conduit 20 can run along a dorsal-radial aspect of the third metacarpal and end in a terminal connection 148.

As shown in FIGS. 11A & 11B, the surgical glove 13 can also include two light sources 16. Each of the light sources 16 can be coupled to a light source conduit 42 and a light source control switch 48. The two light sources 16 can be coupled to distal or distal, dorsal aspects of the index finger and the long finger, respectively. The light source control switch(es) 48 can be located along an ulnar portion of the index finger and/or long finger. The first light source conduit 42 can run from the light source 16 along an ulnar aspect of the index finger and then onto a dorsal surface 150 of the metacarpals (e.g., a dorsal-ulnar aspect of the second metacarpal) and end in a terminal connection 148. The second light source conduit 42 can run from the light source 16 along an ulnar aspect of the long finger and then onto a dorsal surface 150 of the metacarpals (e.g., a dorsal-ulnar aspect of the third metacarpal) and end in a terminal connection 148.

FIG. 12 shows a second sleeve 78 of a gown 30 disclosed herein for use in connection with the complementary glove 13 shown in FIGS. 11A & 11B. Although light source support conduits 43 would be present, as shown in FIG. 1, the connection system 32 of FIG. 12 only shows the irrigation support conduit 69 and the suction support conduit 61 in order to more clearly show the shunt 142. The irrigation support conduit 69 and the suction support conduit 61 can be in controlled fluid communication via the shunt 142. A first portion 144 of the shunt can be in-line with the irrigation support conduit 69, while a second portion 146 of the shunt can be in-line with the suction support conduit 61 The first portion 144 and the second portion 146 of the shunt 142 can each include a three-way stopcock valve (145 & 147, respectively) to control the flow of fluid through the shunt 142. The distal end of each support conduit 61, 69 can include a support connector 149 for coupling to the respective terminal connector 148 at the proximal end of the conduit 15.

FIG. 13 shows a posterior view of an exemplary gown 30 for use in connection with a bilateral surgical systems as described herein. The gown 30 can include a first arm 76 and a second arm 78. Each of the support conduits (e.g., 43, 53, 61 & 69) runs along a back of the arm and shoulder then along the lower back 90 of the gown 30 and can terminate at a distal support connector 154. The support conduits can be secured to the gown 30 by one or more attachment devices 92.

Method of Using Surgical Systems

The invention may also be directed to a method of performing a surgical procedure in which the need to retrieve surgical implements that beforehand were rested on the surgical field is eliminated. In particular, the method may include attaching a first surgical glove 12 to a person conducting the surgical procedure before commencing the surgical procedure. The person conducting the surgical procedure may be, but is not limited to being, a surgeon or other appropriate person. At least one surgical instrument 16, 18, 20, 22 may be attached to the first surgical glove 12 such that the at least one surgical instrument 16, 18, 20, 22 extends proximate to a hand and at or distal to the wrist of the person to which the first surgical glove 12 is attached. The at least one surgical instrument 16, 18, 20, 22 may be nonremovably attached to the glove 12 to prevent the at least one surgical instrument 16, 18, 20, 22, 23 from being removed from the glove 12 during a surgical procedure. The first surgical glove 12 may remain attached to the person throughout the surgical procedure eliminating need to retrieve surgical implements that beforehand were rested on the surgical field. For instance, the surgeon need not rest instruments on the surgical field and constantly pick up the instruments or request the instruments from an assistant. Rather, the instruments may remain attached to the surgeon throughout the duration of the surgery. Such a method enables a surgeon to work more independently and thus maintain focus on the surgical procedure.

The method may also include attaching a second surgical glove 13 to a person conducting the surgical procedure before commencing the surgical procedure. The surgical instrument 16, 18, 20, 22 coupled to the gloves 12, 13 may be at least one light source, at least one suction port, at least one irrigation port, at least one electrical cautery source, at least one ultrasonic cutting and coagulating surgical device, or other appropriate device. The invention is not limited to only these listed devices but may be configured to include other appropriate devices as well to increase the efficiency of the surgical procedure.

Finally, the method also includes using some or all of the surgical instruments 17 by actuating some or all of the switches (e.g., 48, 56, 58, 62, 64, 70 & 140) as part of performing a surgical procedure. The method can include simultaneously and synergistically using at least one surgical instrument 17 on each glove 12 by actuating some or all of the switches (e.g., 48, 56, 58, 62, 64, 70 & 140). The process can also include donning the surgical gown 30 and glove(s) 12, 13 and coupling some or all of the terminal connectors 148 to the respective support connectors 149.

The foregoing is provided for purposes of illustrating, explaining, and describing embodiments of this invention. Modifications and adaptations to these embodiments will be apparent to those skilled in the art and may be made without departing from the scope or spirit of this invention.

The invention claimed is:

1. A surgical system, comprising:
  a surgical glove configured to be removably attached to a human hand, said surgical glove comprising:
  a first surgical instrument attached to the surgical glove, wherein the first surgical instrument is nonremoveably, integrally attached to the surgical glove during formation of the surgical glove, wherein the first surgical instrument is coupled to a finger of the surgical glove;
  a first switch attached to the surgical glove for controlling the first surgical support system; and
  a first actuating element attached to a thumb of the surgical glove, wherein the first actuating element is a discrete element,
  wherein the surgical glove is formed of a latex material or a non-latex material;
  wherein the first switch is actuated when the first actuating element is placed in close proximity to the first switch, and
  wherein a thumb of said surgical glove is free of surgical support systems.

2. The surgical system of claim 1, wherein the surgical glove is formed of the latex material.

3. The surgical system of claim 1, wherein the surgical glove is formed of the non-latex material.

4. The surgical system of claim 1, wherein the first surgical support system is a light source.

5. A surgical system, comprising:
  a glove formed of a latex material, a non-latex material, or a combination thereof, wherein said glove is configured to be removably attached to a human hand, said glove comprising:
  a first surgical support system attached to the glove, wherein the first surgical support system comprises a first surgical instrument and a first conduit, and wherein the first conduit is coupled to a finger of the glove; and
  a first switch attached to the glove for controlling the first surgical support system, said first switch attached to an ulnar surface of the finger of the glove to which the first conduit is coupled.

6. The surgical system of claim 5, wherein the glove is formed of the latex material.

7. The surgical system of claim 5, wherein the glove is formed of the non-latex material.

8. The surgical system of claim 5, wherein the glove is formed of the combination of the latex material and the non-latex material.

9. A surgical system, comprising:
  a surgical glove formed of a latex material, a non-latex material, or a combination thereof, wherein said glove is configured to be removably attached to a human hand, said surgical glove comprising:
  a first surgical support system attached to the surgical glove, wherein the first surgical support system comprises a first surgical instrument and a first conduit, wherein the first surgical instrument is nonremoveably, integrally attached to the surgical glove during the formation of the surgical glove, and wherein the first conduit is coupled to a finger of the surgical glove; and
  a first switch attached to a surface of the surgical glove for controlling the first surgical support system, wherein said first switch is operable by a thumb of a human hand in the surgical glove, and wherein a thumb of said surgical glove is free of said first surgical support systems.

10. The surgical system of claim 9, wherein the glove is formed of the latex material.

11. The surgical system of claim 9, wherein the glove is formed of the non-latex material.

12. The surgical system of claim 9, wherein the glove is formed of the combination of the latex material and the non-latex material.

* * * * *